US010391497B1

United States Patent
Gong et al.

(10) Patent No.: US 10,391,497 B1
(45) Date of Patent: Aug. 27, 2019

(54) DEVICES, METHODS AND SYSTEMS FOR REDUCING SAMPLE VOLUME

(71) Applicant: Theranos, Inc., Palo Alto, CA (US)

(72) Inventors: Xinwei Sam Gong, Palo Alto, CA (US); Daniel Young, Palo Alto, CA (US); William Westrick, Palo Alto, CA (US)

(73) Assignee: Theranos IP Company, LLC, New York, NY (US)

( * ) Notice: Subject to any disclaimer, the term of this patent is extended or adjusted under 35 U.S.C. 154(b) by 0 days.

(21) Appl. No.: 15/161,859

(22) Filed: May 23, 2016

Related U.S. Application Data

(63) Continuation of application No. 14/481,858, filed on Sep. 9, 2014.

(60) Provisional application No. 61/875,678, filed on Sep. 9, 2013, provisional application No. 61/888,318, filed on Oct. 8, 2013, provisional application No. 61/993,566, filed on May 15, 2014.

(51) Int. Cl.
*B01L 3/00* (2006.01)
*G01N 35/00* (2006.01)
*G01N 21/64* (2006.01)

(52) U.S. Cl.
CPC .......... *B01L 3/508* (2013.01); *G01N 21/6428* (2013.01); *G01N 35/00* (2013.01); *B01L 2300/0654* (2013.01); *B01L 2300/0832* (2013.01); *B01L 2300/0848* (2013.01); *G01N 2021/6439* (2013.01); *G01N 2035/00237* (2013.01)

(58) Field of Classification Search
None
See application file for complete search history.

(56) References Cited

U.S. PATENT DOCUMENTS

| 4,021,124 A | | 5/1977 | Sarstedt | |
|---|---|---|---|---|
| 4,310,249 A | * | 1/1982 | Kramer | G01N 21/255 250/228 |
| 6,056,925 A | * | 5/2000 | Sarstedt | B01L 3/5021 422/548 |

OTHER PUBLICATIONS

Office Action dated Oct. 31, 2016 for U.S. Appl. No. 14/481,858.
Office Action dated Aug. 2, 2016 for U.S. Appl. No. 14/481,858.

* cited by examiner

*Primary Examiner* — Xiaoyun R Xu

(57) ABSTRACT

Devices, methods and systems are provided for reducing the sample volume required for analysis. Inserts placed within a sample container, and substitute sample containers having smaller volume sample chambers are provided. Methods are provided for detection and quantification of target substances in reduced volume samples. Methods include placing a small-volume of sample in a small-volume insert. Methods include diluting a small-volume sample, and placing the diluted sample in a small-volume insert. Methods include reducing the volume of sample, and: increasing illumination; increasing dye concentration or amount; increasing the amount of an enzyme substrate; increasing the amounts, concentration, or labeling of antibodies for detection; increasing optical detector sensitivity; increasing the path length of light passing through the sample; decreasing the separation between sample and detector; altering the wavelength, or polarization, or number of wavelengths, passing through the sample; increasing electronic amplification of electrical signals; altering assay temperature; and other alterations.

13 Claims, 3 Drawing Sheets

DEVICES, METHODS AND SYSTEMS FOR REDUCING SAMPLE VOLUME

BACKGROUND

Detection of analytes in a sample and determination of the chemical composition of a sample are useful in many clinical and scientific applications. Thus, methods, devices, and systems for analyzing samples and for detecting target substances within the samples are useful in many contexts. A method of testing for, or for detecting, a target substance in a sample may be termed an "assay." Some assays may be performed by devices or systems with little or no human intervention; such assays may be termed automated assays, and are performed by automatic devices or automatic systems.

Clinical assays are often developed to identify target materials in samples taken from patients. For example, targets may include proteins, nucleic acids, lipids, organic molecules, inorganic molecules and ions. Such target materials may include drugs, drug metabolites, vitamins, hormones, growth factors, carrier proteins, cells, infectious agents, and other target materials that may be indicative of medical conditions or disorders. Other clinical assays may be directed to testing for levels of drugs, drug metabolites, hormones, vitamins, or other substances which may be of therapeutic or clinical interest. In some instances, a sample may include multiple analytes, and multiple assays may be required to detect or quantify all of the analytes of interest in a sample.

Clinical assays require samples to be obtained from a subject, such as a patient suffering from, or suspected of suffering from, a disease characterized by markers identifiable by the assay. However, providing samples is often uncomfortable, or difficult, or inconvenient for a subject; the discomfort, difficulty, and inconvenience is typically greater the larger the volume of sample that is required.

Accordingly, methods and devices for reducing the volume of sample required to be obtained from a subject are desired, and assays, guidelines and methods for altering existing machines and assays that may be performed on smaller volume samples than presently practiced are also desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Analysis of fluid samples typically requires that a volume of sample be held in a container during analysis. Typically a fluid sample is deposited in a tube or other vessel when first obtained from the subject, and then transferred to a container in, or for use in, a sample analysis device. A sample analysis device will have a minimum volume below which a fluid sample is too small for analysis. Applicant discloses herein methods, devices, and systems for reducing the volume of sample required for use in sample analysis devices, including in automatic sample analysis devices. For example, Applicant discloses herein methods, devices, and systems including inserts configured to hold small volumes, including small volumes smaller than the minimum volume otherwise required for analysis in sample analysis devices, including in automatic sample analysis devices. For example, Applicant discloses herein methods, devices, and systems including at least one step of diluting a small-volume sample, effective that the volume of sample used in the assay may be smaller than the minimum volume otherwise required for analysis in sample analysis devices, including in automatic sample analysis devices. For example, Applicant discloses herein methods, devices, and systems including inserts configured to hold small volumes, and including at least one step of diluting a small-volume sample, effective that the volume of sample used in the assay may be smaller than the minimum volume otherwise required for analysis in sample analysis devices, including in automatic sample analysis devices. In embodiments, Applicant discloses herein methods, devices, and systems in which the operation, or structure, or both, of sample analysis devices, including automatic sample analysis devices, are altered effective that small-volume samples may be analyzed, and small signals obtained from such small-volume samples detected and quantified.

In embodiments, Applicant provides methods and devices for modifying assays, and for modifying assay devices, to reduce the volume of sample required for the performance of assays for the detection of analytes. Devices and systems modified according to the methods disclosed herein, and using the devices disclosed herein, are able to perform analytical assays while requiring less sample, providing greater comfort to subjects since smaller samples are less painful to obtain; providing more cost-effective assays and analyses, since smaller sample volumes typically require less reagent volume, and so are less costly to assay; providing less waste pursuant to the assays; and providing other advantages as compared to original assays and methods which require greater sample volumes. Samples, such as blood sample, urine samples, saliva samples, throat-swab samples, nasal-swab samples, or other samples, may be obtained by any means. For example, blood samples may be obtained by venipuncture, finger-stick, or any other means known in the art.

Applicant provides methods for modifying a clinical analysis device comprising reducing the sample volume by placing an insert in a sample container. Applicant provides methods for modifying a sample container used in a clinical analysis device comprising reducing the sample volume by placing an insert in the sample container. Applicant provides methods for modifying sample analysis in a clinical analysis device comprising reducing the sample volume analyzed by the clinical analysis device by placing an insert in the sample container. Applicant provides methods for modifying sample analysis in a clinical analysis device comprising reducing the sample volume analyzed by the clinical analysis device by providing a substitute or replacement sample container having a smaller volume than the original sample container.

Methods for reducing the volume of sample used during, or required for, sample analysis include providing an insert which fits in a sample container effective to reduce the volume of sample held by the combined sample container and insert; or providing a substitute or replacement sample container which has a smaller volume than the original sample container. The sample may be contained within a sample container during at least a portion of the performance of said original assay, said sample container comprising an internal cavity for holding said sample, said internal cavity having a volume, and wherein any of the foregoing methods comprise reducing said volume of said internal cavity. In embodiments, reducing the volume of said internal cavity comprises providing an alternative sample container. In embodiments, reducing the volume of said internal cavity comprises placing an insert into said internal cavity. In embodiments, an insert may comprise an insert cavity configured to hold said sample, wherein said insert cavity comprises a volume less than said internal cavity volume. Thus, in embodiments, an insert is effective to insure that the residual amount of sample remaining in a sample container (after draining the container) comprises only a small volume of sample. In embodiments, an insert may be configured effective to reduce the amount of residual sample volume remaining in the insert in a sample container after draining the insert in the sample container, as compared to the amount of residual sample volume that would remain after draining sample from the sample container in the absence of the insert. In embodiments, an insert may be configured effective that optical signals indicative of the presence of, or quantification of, a target substance in a sample contained within said insert may be detected by said optical detector.

Applicants further provide devices for reducing the volume of sample held within a sample container, wherein said sample container is configured to hold a first volume of sample effective to allow detection of a target substance in said sample by a detector disposed externally to said sample container, wherein said device comprises an insert configured to i) fit within said sample container, ii) hold a second volume of sample, wherein said second volume of sample is less than said first volume of sample, and iii) allow the detection of a signal indicative of the presence of, or quantification of, a target substance in a sample contained within said insert, wherein said detection comprises detection by a detector disposed externally to said sample container. In embodiments, the insert is configured to allow the passage of light effective that optical signals indicative of the presence of, or quantification of, a target substance in a sample contained within said insert may be detected by an optical detector disposed externally to the sample container.

Applicants disclose herein methods of sample analysis comprising reducing the volume of sample used during analysis, by reducing the volume of a cavity in a container used to hold the sample during the performance of the analysis, or during the performance of a portion of the analysis. Applicants disclose herein methods of sample analysis comprising reducing the dead volume of a container used to hold the sample during the performance of the analysis, or during the performance of a portion of the analysis.

Applicants disclose a method of sample analysis with a sample analysis device, wherein the sample is contained within a sample container comprising an internal cavity for holding said sample, said internal cavity having a volume of less than about 500 µL, or less than about 400 µL, or less than about 300 µL, or less than about 250 µL, or less than about 200 µL, or less than about 150 µL, or less than about 100 µL, or less than about 50 µL, or less than about 25 µL, or less than about 15 µL, or less than about 10 µL, or less than about 5 µL, or less than about 4 µL, or less than about 3 µL, or less than about 2 µL, or less than about 1 µL, or less, the method comprising: placing a sample within said internal cavity of said sample container, and performing the sample analysis.

Applicants disclose a method of sample analysis with a sample analysis device, wherein the sample is contained within a sample container comprising an internal cavity for holding said sample, and wherein the internal cavity has a dead volume of less than about 200 µL, less than about 100 µL, or less than about 50 µL, or less than about 30 µL, or less than about 20 µL, or less than about 15 µL, or less than about 10 µL, or less than about 5 µL, or less than about 4 µL, or less than about 3 µL, or less than about 2 µL, or less than about 1 µL, or less, the method comprising placing a sample within said internal cavity of said sample container, and performing the sample analysis.

In embodiments of the methods of sample analysis disclosed herein, the sample containers, or inserts placed therein, comprise internal cavities comprising a bevel in the bottom portion of an insert cavity, wherein the cross-sectional shape of said bevel comprises a triangular, circular, hemispherical, oval, elliptical, or other shape. In embodiments of the methods of sample analysis disclosed herein, the sample containers, or inserts placed therein, comprise internal cavities comprising an angle effective to provide a taper in at least an upper portion, or a lower portion, or both, of a wall of said internal cavity, wherein the taper comprises tapers selected from tapers in which the upper taper the same as the lower taper; the upper taper is different than the lower taper; tapers which become narrower towards the lower portion; and tapers which become wider towards the lower portion. In embodiments of the methods of sample analysis disclosed herein, the sample containers, or inserts placed therein, comprise internal cavities comprising a bevel, a wall, a floor, and a wall angle formed by said wall and said bevel, wherein the wall angle comprises an angle of between about 80° to about 40°, or between about 65° to about 45°; in further embodiments, the internal cavity comprises a floor angle formed by the floor and the bevel, and the wall angle is complementary to the floor angle.

In embodiments of the methods of sample analysis disclosed herein, the sample containers, or inserts placed therein, comprise internal cavities comprising a depth and a width, wherein the ratio of the depth to the width is between about 0.1:1 to about 10:1; between about 0.2:1 to about 5:1; or between about 0.5:1 to about 3:1; or may be about 0.3:1; or may be about 0.5:1; or may be about 0.8:1; or may be about 1:1; or may be about 1.2:1; or may be about 1.5:1; or may be about 1.8:1; or may be about 2:1; or may be about 3:1; or may be about 4:1; or may be about 5:1; or may be about 6:1; or may be about 8:1; or may be another ratio.

In embodiments of the methods of sample analysis disclosed herein, the internal cavity comprises an internal cavity selected from the group consisting of the internal cavity of an insert, wherein said insert is disposed within the cavity of an original sample container; the internal cavity of a replacement sample container; and the internal cavity of another sample container.

In embodiments of the methods of sample analysis disclosed herein, the sample that is analyzed may comprise a portion of sample that was obtained from a subject. Thus, a small volume of sample may be obtained by obtaining a small-volume sample from a subject, or by obtaining a small volume aliquot of a sample (which sample may itself be a small-volume sample). In embodiments, small volumes of sample may be diluted to provide larger total volumes for analysis, e.g., for analysis in automatic sample analysis devices or automatic sample analysis systems. Such dilution may be performed prior to placing the sample, or aliquot thereof, in an automatic sample analysis device or system; or may be performed by or within an automatic sample analysis device or system prior to analysis of the sample or aliquot thereof.

In embodiments, the methods are performed on diluted samples, or aliquots thereof, and comprise modifications of one or more steps of such assays, where such modifications take into account differences in sample volume and concentration, or differences in reagent volume or concentration, or both, as compared to such assays and assays steps otherwise configured for use with samples that have not been diluted. Thus, for example, one or more steps of assays suitable for use with samples that have not been diluted may be modified for use with diluted samples, or aliquots of diluted samples. An amount of dilution may be defined by a ratio of (diluted volume):(original volume). In embodiments, a dilution of a sample, including dilution of a small-volume fluid sample, may be dilution that is greater than about 2:1; or greater than about 3:1; or greater than about 4:1; or greater than about 5:1; or greater than about 10:1; or greater than about 20:1; or greater than about 30:1; or greater than about 40:1; or greater than about 50:1; or greater than about 100:1; or greater than about 200:1; or greater than about 300:1; or greater than about 400:1; or greater than about 500:1; or greater than about 1000:1; or greater than about 2000:1; or greater than about 4000:1; or greater than about 5000:1; or greater than about 10000:1; or greater.

In embodiments, modification of a step or steps may include, without limitation, modification of the duration or timing of a step (e.g., delay before performing a step, or duration of a step, or other time parameter associated with a step); may include modification of the sequence (e.g., ordering) of steps; may include deleting a step or combining two or more steps together; may include modification of detection method, intensity of illumination, incubation temperature, reaction temperature, or other parameter or combination of parameters of one or more steps of an assay. In embodiments, for example, one or more reagents for use in assays suitable for use with samples that have not been diluted may be modified for use with diluted samples, or aliquots of diluted samples. In embodiments, modification of a reagent or reagents may include without limitation, modification of the concentration(s) of one or more constituent(s) of the reagent; may include the combination of two or more reagents; may include elimination of one or more constituent(s) of the reagent; may include adding one or more constituent(s) to the reagent; may include modification of the ratio of concentration(s) of two or more constituent(s) of the reagent; or other modifications.

An automatic sample analysis device or system may be modified, e.g., by providing an insert, to accept a small-volume sample, or aliquot of a sample, and to analyze the sample or aliquot for the presence or absence of an analyte, or of a plurality of analytes. In embodiments, an automatic sample analysis device or system may analyze such a sample, or a calibration reagent, or both. A sample, or aliquot thereof, may be diluted when provided to an automatic sample analysis device or system. A sample, or aliquot thereof, may be provided undiluted to an automatic sample analysis device or system. A sample, or aliquot thereof, may be diluted by an automatic sample analysis device or system. A calibration reagent may be provided undiluted to an automatic sample analysis device or system, or may be diluted to the same extent as a diluted sample when provided to an automatic sample analysis device or system. A calibration reagent may be diluted by an automatic sample analysis device or system for use with a diluted sample; when diluted, a calibration reagent is diluted to the same extent as a diluted sample, or in a known ratio or known relation to the amount of dilution of the sample.

Applicant discloses methods of analyzing a small-volume fluid sample with a sample analysis device having a sample container configured for use with a fluid sample having a volume of no less than a first volume, wherein said small-volume sample has a second volume smaller than said first volume, wherein analysis by said sample analysis device requires that a sample be held within said sample container during at least a portion of the performance of said analysis, the sample container having an internal cavity having an original volume, the methods comprising: Placing an insert within said internal cavity of the sample container, wherein said insert has an insert cavity having a volume of less than said original volume, and wherein said insert cavity is configured to hold a small-volume fluid sample, Placing said small-volume fluid sample within said insert cavity, and Analyzing the small-volume sample with said sample analysis device.

Applicant discloses methods of analyzing a small-volume fluid sample with a sample analysis device having a sample container configured for use with a fluid sample having a volume of no less than a first volume, wherein said small-volume sample has a second volume smaller than said first volume, wherein analysis by said sample analysis device requires that a sample be held within said sample container during at least a portion of the performance of said analysis, the sample container having an internal cavity having an original volume, the methods comprising: Placing an insert within said internal cavity of the sample container, wherein said insert comprises an insert cavity for holding said sample having a volume of less than said original volume, said insert cavity comprising a bevel, a wall, a floor, and a wall angle formed by said wall and said bevel, wherein the wall angle comprises an angle of between about 80° to about 40°, or between about 65° to about 45°, Placing said small-volume fluid sample within said insert cavity, and Analyzing the small-volume sample with said sample analysis device. In embodiments, such a method further comprises diluting said small-volume fluid sample prior to placing the small-volume fluid sample in the insert cavity of said insert, wherein said dilution is effective to increase the volume of the diluted sample to a third volume, wherein said third volume is greater than said second volume. In embodiments, where dilution is defined by a ratio of (diluted volume):(original volume), such a dilution may be dilution greater than about 2:1; or greater than about 3:1; or greater than about 4:1; or greater than about 5:1; or greater than about 10:1; or greater than about 20:1; or greater than about 30:1; or greater than about 40:1; or greater than about 50:1; or greater than about 100:1; or greater than about 200:1; or greater than about 300:1; or greater than about 400:1; or greater than about 500:1; or greater than about 1000:1; or greater than about 2000:1; or greater than about 4000:1; or greater than about 5000:1; or greater than about 10000:1; or greater.

In embodiments, the insert cavity has a dead volume, wherein the dead volume has a volume less than about 200 μL, or less than about 100 μL, or less than about 50 μL, or less than about 30 μL, or less than about 20 μL, or less than about 15 μL, or less than about 10 μL, or less than about 5 μL, or less than about 4 μL, or less than about 3 μL, or less than about 2 μL, or less than about 1 μL. In embodiments, the insert cavity comprises a depth and a width, wherein the ratio of the depth to the width is between about 0.1:1 to about 10:1; between about 0.2:1 to about 5:1; or between about 0.5:1 to about 3:1; or may be about 0.3:1; or may be about 0.5:1; or may be about 0.8:1; or may be about 1:1; or may be about 1.2:1; or may be about 1.5:1; or may be about 1.8:1; or may be about 2:1; or may be about 3:1; or may be about 4:1; or may be about 5:1; or may be about 6:1; or may be about 8:1. In embodiments, the insert cavity comprises a bevel in the bottom portion of said insert cavity, wherein the cross-sectional shape of said bevel comprises a triangular, circular, hemispherical, oval, or elliptical shape. In embodiments, the insert cavity comprises a depth and a width, wherein the ratio of the depth to the width is between about 0.1:1 to about 10:1; between about 0.2:1 to about 5:1; or between about 0.5:1 to about 3:1; or may be about 0.3:1; or may be about 0.5:1; or may be about 0.8:1; or may be about 1:1; or may be about 1.2:1; or may be about 1.5:1; or may be about 1.8:1; or may be about 2:1; or may be about 3:1; or may be about 4:1; or may be about 5:1; or may be about 6:1; or may be about 8:1.

Applicant discloses methods of analyzing a small-volume fluid sample with a sample analysis device having a sample container configured for use with a fluid sample having a volume of no less than a first volume, wherein said small-volume sample has a second volume smaller than said first volume, wherein analysis by said sample analysis device requires that a sample be held within said sample container during at least a portion of the performance of said analysis, the sample container having an internal cavity having an original volume, the methods comprising: Diluting said small-volume fluid sample prior to placing the small-volume fluid sample in the insert cavity of said insert, wherein said dilution is effective to increase the volume of the diluted sample to a third volume, wherein said third volume is greater than said second volume, Placing an insert within said internal cavity of the sample container, wherein said insert comprises an insert cavity for holding said sample having a volume of less than said original volume, said insert cavity comprising a bevel, a wall, a floor, and a wall angle formed by said wall and said bevel, wherein the wall angle comprises an angle of between about 80° to about 40°, or between about 65° to about 45°, Placing said small-volume fluid sample within said insert cavity, and Analyzing the small-volume sample with said sample analysis device.

In embodiments of the methods of sample analysis disclosed herein, sample analysis may comprise processing a sample, analyzing a sample, or both processing a sample and analyzing a sample.

Applicant provides methods for modifying a clinical analysis device comprising reducing the sample volume by placing an insert in a sample holder. Applicant provides methods for modifying a clinical analysis device comprising reducing the sample volume by placing an insert in a sample holder, and increasing the sensitivity of a detector. Applicant provides methods for modifying a clinical analysis device comprising reducing the sample volume by placing an insert in a sample holder, and decreasing the distance between a sample and a detector. Applicant provides methods for modifying a clinical analysis device comprising reducing the sample volume by placing an insert in a sample holder, and increasing the intensity of an illumination source providing illumination of a sample to be detected by a detector. Applicant provides methods for modifying a clinical analysis device comprising reducing the volume of a sample container by placing an insert into said sample container; and increasing the concentration of a dye or of a substrate which is detected by, or which provides a signal detected by, a detector during operation of the device. Applicant provides methods for modifying a clinical analysis device comprising diluting a sample, and: increasing the sensitivity of a detector; or increasing the intensity of an illumination source providing illumination of a sample to be detected by a detector; or increasing the concentration of a dye/substrate which is detected by a detector during operation of the device.

Accordingly, Applicant provides a method for reducing the volume of sample used in the performance of an assay as compared to an original volume of sample used for the original performance of said assay, wherein said assay comprises the detection of an optical signal for detection of the presence of, or quantification of, a target substance in a sample, the method comprising:

Reducing the volume of sample used in the assay from a first sample volume to a second sample volume, wherein said second sample volume is less than said first sample volume, and wherein the assay was originally performed using said first volume of sample; and Increasing the intensity of illumination applied to said sample, as compared to the original intensity of illumination applied to the sample, wherein said illumination is used to detect the presence of said target substance in the sample, or to quantify the amount of said target substance in the sample.

Applicants further provide a method for reducing the volume of sample used in the performance of an assay as compared to an original volume of sample used for the original performance of said assay, wherein said assay comprises the detection of a fluorescent label for detection of the presence of, or quantification of, a target substance in a sample, the method comprising:

Reducing the volume of sample used in the assay from a first sample volume to a second sample volume, wherein said second sample volume is less than said first sample volume, and wherein the assay was originally performed using said first volume of sample; and Increasing the intensity of light illuminating the sample and assay reagents during fluorescence measurements, as compared to the original intensity of light illuminating the sample and assay reagents during fluorescence measurements, wherein said fluorescence measurements are used to detect the presence of said target substance in the sample, or to quantify the amount of said target substance in the sample.

Applicants further provide a method for reducing the volume of sample used in the performance of an assay as compared to an original volume of sample used for the original performance of said assay, wherein said assay comprises the detection of a dye for detection of the presence of, or quantification of, a target substance in a sample, the method comprising:

Reducing the volume of sample used in the assay from a first sample volume to a second sample volume, wherein said second sample volume is less than said first sample volume, and wherein the assay was originally performed using said first volume of sample; and Increasing the concentration of dye added to the sample, as compared to the original concentration of dye added to the sample, wherein said dye labels a target substance in the sample. In embodiments, increasing the concentration of a dye added to the sample comprises increasing the amount of dye added to the sample, as compared to the original amount of dye added to the sample.

Applicants further provide a method for reducing the volume of sample used in the performance of an assay as compared to an original volume of sample used for the original performance of said assay, wherein said assay comprises the detection of an enzymatic label for detection of the presence of, or quantification of, a target substance in a sample, the method comprising:

Reducing the volume of sample used in the assay from a first sample volume to a second sample volume, wherein said second sample volume is less than said first sample volume, and wherein the assay was originally performed using said first volume of sample; and Increasing the concentration of substrate added to the sample in the presence of the enzyme prior to, or during, enzymatic label measurements, as compared to the original concentration of substrate added to the sample, wherein said enzymatic label measurements are indicative of the presence of, or quantities of, target substance in the sample.

Applicants further provide a method for reducing the volume of sample used in the performance of an assay as compared to an original volume of sample used for the original performance of said assay, wherein said assay comprises the detection of a labeled antibody for detection of the presence of, or quantification of, a target substance in a sample, the method comprising:

Reducing the volume of sample used in the assay from a first sample volume to a second sample volume, wherein said second sample volume is less than said first sample volume, and wherein the assay was originally performed using said first volume of sample; and Increasing the concentration of labeled antibody added to the sample, as compared to the original concentration of labeled antibody added to the sample, wherein said antibody binds a target substance in the sample. In embodiments, increasing the concentration of a labeled antibody added to the sample comprises increasing the amount of labeled antibody added to the sample, as compared to the original amount of labeled antibody added to the sample.

Applicants further provide a method for reducing the volume of sample used in the performance of an assay as compared to an original volume of sample used for the original performance of said assay, wherein said assay comprises the detection of a labeled antibody for detection of the presence of, or quantification of, a target substance in a sample, the method comprising:

Reducing the volume of sample used in the assay from a first sample volume to a second sample volume, wherein said second sample volume is less than said first sample volume, and wherein the assay was originally performed using said first volume of sample; and Increasing the number of labels per labeled antibody added to the sample, as compared to the original number of labels per labeled antibody added to the sample, wherein said antibody binds a target substance in the sample.

Applicants further provide a method for reducing the volume of sample used in the performance of an assay as compared to an original volume of sample used for the original performance of said assay, wherein said assay comprises the detection of an optical signal produced by a target substance, or by a reagent which binds to or reacts with said target substance, the assay being useful for detection of the presence of, or quantification of, the target substance in a sample, the method comprising:

Reducing the volume of sample used in the assay from a first sample volume to a second sample volume, wherein said second sample volume is less than said first sample volume, and wherein the assay was originally performed using said first volume of sample; and Increasing the sensitivity of an optical detector used to detect said optical signal, as compared to the original sensitivity of the optical detector used to detect the optical signal.

Applicants further provide a method for reducing the volume of sample used in the performance of an assay as compared to an original volume of sample used for the original performance of said assay, wherein said assay comprises the detection of an optical signal produced by a target substance, or by a reagent which binds to or reacts with said target substance, the assay being useful for detection of the presence of, or quantification of, the target substance in a sample, the method comprising:

Reducing the volume of sample used in the assay from a first sample volume to a second sample volume, wherein said second sample volume is less than said first sample volume, and wherein the assay was originally performed using said first volume of sample; and Decreasing the separation between the sample and an optical detector used to detect said optical signal, as compared to the original separation between the sample and the optical detector used to detect the optical signal.

Applicants further provide a method for reducing the volume of sample used in the performance of an assay as compared to an original volume of sample used for the original performance of said assay, wherein said assay comprises the detection of an optical signal produced by a target substance, or by a reagent which binds to or reacts with said target substance, the assay being useful for detection of the presence of, or quantification of, the target substance in a sample, the method comprising:

Reducing the volume of sample used in the assay from a first sample volume to a second sample volume, wherein said second sample volume is less than said first sample volume, and wherein the assay was originally performed using said first volume of sample; and Increasing the path length within the sample between a source of illumination and through the sample to an optical detector used to detect said optical signal, as compared to the original path length within the sample between a source of illumination and through the sample to an optical detector used to detect the optical signal. In embodiments, the path length within the sample is increased, as compared to the original path length within the sample, by alteration of the container holding the sample. In further embodiments, the path length within the sample is increased, as compared to the original path length within the sample, by reflection or refraction of light within the container holding the sample.

Applicants further provide a method for reducing the volume of sample used in the performance of an assay as compared to an original volume of sample used for the original performance of said assay, wherein said assay comprises the detection of an optical signal produced by a target substance, or by a reagent which binds to or reacts with said target substance, the assay being useful for detection of the presence of, or quantification of, the target substance in a sample, the method comprising:

Reducing the volume of sample used in the assay from a first sample volume to a second sample volume, wherein said second sample volume is less than said first sample volume, and wherein the assay was originally performed using said first volume of sample; and Altering the wavelength of light passing through said sample and to an optical detector used to detect the optical signal, as compared to the original wavelength of light passing through the sample and to an optical detector used to detect the optical signal. In embodiments, altering the wavelength of light passing through said sample and to an optical detector used to detect the optical signal comprises providing multiple wavelengths of light passing through the sample and to an optical detector.

Applicants further provide a method for reducing the volume of sample used in the performance of an assay as compared to an original volume of sample used for the original performance of said assay, wherein said assay comprises the detection of an optical signal produced by a target substance, or by a reagent which binds to or reacts with said target substance, the assay being useful for detection of the presence of, or quantification of, the target substance in a sample, the method comprising:

Reducing the volume of sample used in the assay from a first sample volume to a second sample volume, wherein said second sample volume is less than said first sample volume, and wherein the assay was originally performed using said first volume of sample; and Altering the polarization of light passing through said sample and to an optical detector used to detect the optical signal, as compared to the original polarization of light passing through the sample and to an optical detector used to detect the optical signal. Applicants further provide a method for reducing the volume of sample used in the performance of an assay as compared to an original volume of sample used for the original performance of said assay, wherein said assay comprises the detection of an electrical signal indicative of the presence of, or quantification of, the target substance in a sample, the method comprising:

Reducing the volume of sample used in the assay from a first sample volume to a second sample volume, wherein said second sample volume is less than said first sample volume, and wherein the assay was originally performed using said first volume of sample; and Increasing the electronic amplification of said electrical signal, as compared to the original electronic amplification of the electrical signal. In embodiments, the electrical signal is produced by the target substance, or by a reagent which binds to or reacts with said target sub stance.

Applicants further provide a method for reducing the volume of sample used in the performance of an assay as compared to an original volume of sample used for the original performance of said assay, wherein said assay comprises the detection of a signal indicative of the presence of, or quantification of, the target substance in a sample, wherein said signal comprise a temperature-sensitive signal, the method comprising:

Reducing the volume of sample used in the assay from a first sample volume to a second sample volume, wherein said second sample volume is less than said first sample volume, and wherein the assay was originally performed using said first volume of sample; and Altering the temperature of the assay. In embodiments, the temperature-sensitive signal is increased with increasing temperature, and wherein altering the temperature of the assay comprises increasing the temperature of the assay. In further embodiments, the temperature of said original performance of said assay was near 20° C., and wherein said altered assay temperature is selected from about 25° C., about 30° C., about 32° C., about 34° C., about 35° C., about 36° C., about 37° C., about 38° C., about 39° C., and about 40° C.

In any of the foregoing methods, the sample may be contained within a sample container during at least a portion of the performance of said original assay, said sample container comprising an internal cavity for holding said sample, said internal cavity having a volume, and wherein any of the foregoing methods comprise reducing said volume of said internal cavity. In embodiments, reducing the volume of said internal cavity comprises providing replacement sample container, or an alternative (e.g., a substitute) sample container. In embodiments, reducing the volume of said internal cavity comprises placing an insert into said internal cavity. In embodiments, an insert may comprise an insert cavity configured to hold said sample, wherein said insert cavity comprises a volume less than said internal cavity volume. In embodiments, an insert may comprise an insert cavity configured to retain less sample after draining as compared to the amount of sample retained in an original sample container after draining. In embodiments, an insert may be configured effective that optical signals indicative of the presence of, or quantification of, a target substance in a sample contained within said insert may be detected by said optical detector.

In embodiments, a detector may be disposed outside a sample container, e.g., disposed in a location that is external to the sample container. For example, an optical detector may be disposed in a location that is external to a sample container. In embodiments, a detector may be disposed, at least partially, within a sample container, e.g., a tip portion, or other portion, disposed within a sample container (e.g., within an insert cavity of a sample container). In embodiments, a fiber-optical conduit may direct light to an optical detector; such a fiber-optical conduit may have an end, e.g., a tip, that is configured to receive light emitted from, or passing through, a sample container. In embodiments, a fiber-optical conduit may have an end, e.g. a tip, that is disposed outside of a sample container, e.g., in a location that is external to the sample container. In embodiments, a fiber-optical conduit may have an end, e.g. a tip, that is disposed within a sample container, e.g., within an insert cavity of a sample container. In embodiments, a fiber-optical conduit may have an end, e.g. a tip, that is disposed at least partially within a sample container, e.g., at least partially within an insert cavity of a sample container.

Applicants disclose herein devices for reducing the volume of sample held within a sample container, wherein the sample container is configured to hold a first volume of sample effective to allow detection of a target substance in the sample by a detector disposed externally to the sample container, wherein the device comprises an insert configured to i) fit within the sample container, ii) hold a second volume of sample, wherein the second volume of sample is less than the first volume of sample, and iii) allow the detection of a signal indicative of the presence of, or quantification of, a target substance in a sample contained within the insert, wherein the detection comprises detection by a detector, wherein at least a portion of the detector is disposed within the sample container. For example, such a detector may have a tip portion, and the tip portion of the detector may be disposed inside the sample container. In embodiments, such a detector may be, for example, an ion-selective electrode (e.g., a sodium selective electrode, a potassium-selective electrode, a chloride-selective electrode, or other ion-selective electrode); a voltammetric probe; a amperometric probe; or other detector configured to be placed within the sample container, or configured for at least a portion of the detector, to be placed within the sample container.

Practice of these methods provides surprising results. For example, devices designed to use large volume samples (e.g., volumes on the order of tens of milliliters, or even on the order of one or a few milliliters) may be modified to provide results using only small fractions of a milliliter, or even only a few microliters of sample. Practice of the methods disclosed herein, and use of the devices disclosed herein, allows detection of target analytes in very small samples; this is surprising since previously available devices, systems, assays, and techniques required much larger sample volumes. In addition, use of small-volume samples may allow detection of target analytes within short periods of time, including within periods of time shorter than the times required using unmodified devices and systems.

Accordingly, improved methods for detecting, identifying, characterizing, and measuring one or more analytes in a sample in an automatic sample analysis device are provided. In embodiments, the improved methods provide improved methods for detecting, identifying, characterizing, and measuring one or more analytes in a diluted sample, or in multiple portions of a diluted sample, in an automatic sample analysis device. In embodiments, these methods may be performed in a short period of time, and may be performed on small-volume samples. The methods disclosed herein provide advantages by requiring only a small amount of sample to be collected from a subject; by requiring only a short period of time perform an assay; by performing multiple assays from a single sample; by performing multiple assays in a single automatic sample analysis device; and by providing other advantages and improvements.

Practice of these methods provides advantages over previous methods and devices by requiring smaller volumes of reagents as well as smaller volumes of sample. Thus, the methods and devices disclosed herein provide synergistic advantages, in that by reducing the sample volume required, reagent volumes are also reduced, assay cost is reduced, discomfort to the subject (from whom the sample is obtained) is reduced, and waste resulting from the performance of the assays is reduced. Accordingly, the present methods and devices are useful and provide surprising advantages for assays for detecting analytes in a sample.

DETAILED DESCRIPTION

Figure 1:
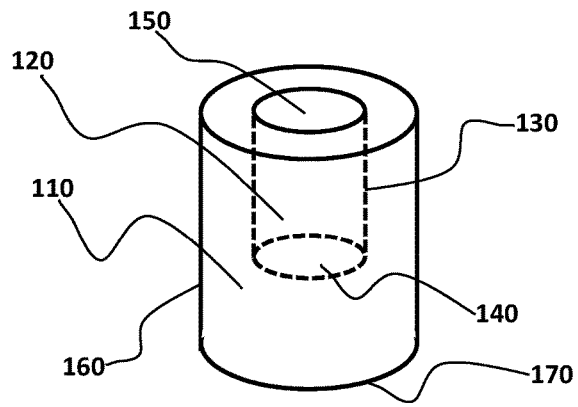
FIG. 1 provides an illustration of an insert configured to fit within a sample container.

Description and disclosure of examples of reagents, assays, methods, kits, devices, and systems which may be used with the methods, assays, reagents, devices and systems disclosed herein may be found, for example, in U.S. Patent Application Ser. No. 61/993,566 filed May 15, 2014; U.S. Patent Application Ser. No. 61/888,318 filed Oct. 8, 2013; U.S. Patent Application Ser. No. 61/875,678 filed Sep. 9, 2013; U.S. Patent Application Ser. No. 61/858,589 filed Jul. 25, 2013; U.S. Pat. Nos. 8,380,541; 8,088,593; U.S. patent application Ser. No. 13/769,798, filed Feb. 18, 2013; U.S. patent application Ser. No. 13/769,779, filed Feb. 18, 2013; PCT/US2012/57155, filed Sep. 25, 2012; U.S. patent application Ser. No. 13/244,949, filed Sep. 26, 2011; U.S. Patent Application Ser. No. 61/800,606, filed Mar. 15, 2013; U.S. Patent Application Ser. No. 61/766,095, filed Feb. 18, 2013; and U.S. Patent Application Ser. No. 61/673,245, filed Sep. 26, 2011, the disclosures of which patents and patent applications are all hereby incorporated by reference in their entireties.

Definitions

As used herein, the term "original volume" and grammatical variants thereof refer to the sample volume used in an assay, or in an assay device, prior to modification or alteration of the assay method, or assay device.

As used herein, the term "reduced volume" and grammatical variants thereof refer to the sample volume used in an assay, or in an assay device, following modification or alteration of the assay method, or assay device, where such modification and alteration reduce the sample volume as compared to the original volume.

As used herein, the term "dead volume" and grammatical variants thereof refer to the residual volume of sample remaining in a container after the container has been drained of sample by normal operation of a device or system; thus, the portion of a sample that effectively cannot be removed from a sample container (or insert cavity placed in a sample container) by normal operation of a device or system, or by normal methods, comprises the dead volume of that sample container or insert. (Although application of high pressure air or steam, or extraction with a series of solvents, or other heroic measures (which typically destroy the sample and analytes in it) might "remove" more of the sample, the need for such methods to remove the remaining sample indicates that the remaining sample indeed effectively cannot be removed by normal operations or methods.)

Thus, a volume of sample may remain in a sample container after draining the container. Applicants disclose herein methods and devices which are useful for reducing the volume of sample which remains after draining, e.g., to a small volume of sample.

Thus, as disclosed herein, it is desirable to reduce the amount of sample remaining in a sample container (after draining the container) to a small volume of sample. In embodiments, such a small volume of sample may comprise less than about 50 µL, less than about 40 µL, less than about 30 µL, or less than about 25 µL, less than about 20 µL, or less than about 15 µL, or less than about 10 µL, or less than about 5 µL, or less than about 4 µL, or less than about 3 µL, or less than about 2 µL, or less than about 1 µL, or less.

The word "label" or "marker" or the phrases "detectable label" and "marker moiety" when used herein refer to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable. A label may be, without limitation, a dye, an epitope tag, a fluorescent moiety, a luminescent moiety, a chemiluminescent moiety, an enzymatic label, a magnetic label, a paramagnetic label, a contrast agent, a nanoparticle, a radioisotope, biotin, streptavidin, and a quencher.

A label may be an alkaline phosphatase label, in which the results of a reaction catalyzed by alkaline phosphatase is observed, and may be used to identify an analyte or verify its presence in a sample, and may be used to quantify an analyte in a sample. Alkaline phosphatase reagents are commercially available; for example, Nitroblue Tetrazolium (NBT) is used with the alkaline phosphatase substrate 5-Bromo-4-Chloro-3-Indolyl Phosphate (BCIP) to provide a colored product which may be observed and quantitated. Other reagents include Fast Red TR/Naphthol AS-MX and TR phosphate (4-Chloro-2-methylbenzenediazonium/3-Hydroxy-2-naphthoic acid 2,4-dimethylanilide phosphate, reagents for the production of p-nitrophenol, and others.

For example, a label may be a peroxidase label (such as horseradish peroxidase, myeloperoxidase, or other peroxidase) in which the results of a reaction catalyzed by the peroxidase is observed, and may be used to identify an analyte or verify its presence in a sample, and may be used to quantify an analyte in a sample. Benzidine-containing compounds (e.g., diaminobenzidine, tetramethyl benzidine), aniline-containing compounds, aminoantipyrene compounds, Trinder reagents, and other reagents known in the art may be used to provide a detectable product in the presence of a peroxidase.

A label may be a dye, such as rhodamine and related rhodamine dyes (e.g., tetramethylrhodamine (FMR), carboxytatramethyl rhodamine (TAMRA), and others), fluorescein and fluorescein derivatives (e.g., 5-carboxyfluorescein, 6-carboxy fluorescein and others), phycoerythrin, umbelliferone, Texas Red, rare earth chelates (europium chelates), dansyl dyes (including, e.g., dansylamide dyes, dansyl cadaverine, dansyl chloride, and others); cyanine dyes (e.g., Cy3, Cy5, SYBR green, and others); Lissamine; phycoerythrins; Texas Red; and analogs thereof.

A label may be a fluorescent material, including fluorescent dyes, and including green fluorescent protein and other fluorescent proteins known in the art. A label may be a luminescent moiety, such as luminol, or other luminescent material, including bioluminescent materials such as luciferase, luciferin, and aequorin.

A label may be a nanoparticle, such as a gold nanoparticle (e.g., a colloidal gold particle), or a quantum dot (e.g., a small particle, typically a semiconductor, which may be detectable upon application of an appropriate amount and wavelength of electromagnetic radiation, e.g., by illumination). A label may be a magnetic label, or a paramagnetic label, which may be a nanoparticle or bead. A label may be a radioisotope or other radioactive material, including, e.g., $^{131}$I, $^{125}$I, $^{111}$In, $^{99}$Tc, $^{35}$S, $^{14}$C, and $^{3}$H.

The term "quench" or "quenching" is used to indicate a reduction in detectable emission radiation, e.g., fluorescent or luminescent radiation, from a source that would otherwise have emitted this radiation. Quenching is a reduction of at least 50%, preferably 80% and more preferably 90%, of the detectable radiation from the source.

The term "quenchable dye" as used herein is a single molecular species that emits detectable radiation when in solution or bound to a single-stranded oligomer, either directly or through a linking moiety. The detectable radiation of a quenchable dye bound directly to a single-stranded oligomer is reversibly quenched upon hybridization of the oligomer to a complementary oligonucleotide to form a hybrid duplex or triplex. No additional molecular species, e.g., a quenching dye, is required for the quenching to occur. However, if the quenchable dye is bound to the oligomer through a linker moiety, hybridization of the oligomer to its complement will not result in quenching of the detectable radiation emitted by the dye.

Fluorescent dyes that intercalculate with double-stranded DNA include, for example, SYBR Gold™, SYBR Green I™, SYBR Green II™, ethidium bromide, BlueView™ methylene blue, DAPI, DRAQ5 and related dyes, and acridine orange. Other fluorophores include, but are not limited to 7-dimethylaminocoumarin-3-carboxylic acid, dansyl chloride, nitrobenzodiazolamine (NBD), dabsyl chloride, cinnamic acid, fluorescein carboxylic acid, Nile Blue, tetramethylcarboxyrhodamine, tetraethylsulfohodamine, 5-carboxy-X-rhodamine (5-ROX), and 6-carboxy-X-rhodamine (6-ROX). Quenchers that may be used include, for example, DDQ-I, DDQ-II (Eurogentec), Eclipse (Epoch Biosciences), Iowa Black FQ, Iowa Black RQ (Integrated DNA Technologies), BHQ-1, BHQ-2, BHQ-3 (Biosearch Technologies), QSY-7, QSY-21 (Molecular Probes), and Dabcyl.

Dyes include, for example, CAL Fluor Gold, CAL Fluor Orange, Quasar 570, CAL Fluor Red 590, CAL Fluor Red 610, CAL Fluor Red 610, CAL Fluor Red 635, Quasar 670 (Biosearch Technologies), VIC, NED (Life Technologies), Cy3, Cy5, Cy5.5 (GE Healthcare Life Sciences), Oyster 556, Oyster 645 (Integrated DNA Technologies), LC red 610, LC red 610, LC red 640, LC red 670, LC red 705 (Roche Applies Science), Texas red, FAM, TET, HEX, JOE, TMR, and ROX. Non-limiting examples of near infrared dyes that can be conjugated to the antibodies, fragments, and/or derivatives of the presently disclosed subject matter include NIR641, NIR664, NIT7000, and NIT782. fluorescent label including, but not limited to Cy3, Cy5, Cy7, and any of the ALEXA FLUOR® series of fluorescent labels.

Signals indicative of the presence or absence, or of the amount, of an analyte or of multiple analytes in a sample, may be optical signals. Optical signals may be detected, and may be measured, by optical detectors, which may include spectrophotometers, photomultiplier tubes, charge-coupled devices, photodiodes, avalanche photodiodes, avalanche photodiode arrays, pin diodes, digital cameras, and other optical devices and optical detection means.

As used herein, the term "antibody" is used in the broadest sense and specifically covers single monoclonal antibodies (including agonist and antagonist antibodies) and antibody compositions with polyepitopic specificity. Thus, antibodies may be polyclonal antibodies, e.g., may be antibodies purified from the blood of an animal such as a sheep or goat which has been challenged by a target antigen, and may be monoclonal antibodies. For example, monoclonal antibodies may be made by the hybridoma method first described by Kohler et al., Nature, 256:495 (1975), or may be made by recombinant DNA methods (see, e.g., U.S. Pat. No. 4,816,567 to Cabilly et al.). The "monoclonal antibodies" also include clones of antigen-recognition and binding-site containing antibody fragments (Fv clones) isolated from phage antibody libraries using the techniques described in Clackson et al., Nature, 352:624-628 (1991) and Marks et al., J. Mol. Biol., 222:581-597 (1991), for example. Monoclonal antibodies are obtained from a population of substantially homogeneous antibodies, i.e., the individual antibodies comprising the population are identical except for possible naturally-occurring mutations that may be present in minor amounts.

Antibodies (e.g., IgG antibodies) are usually heterotetrameric glycoproteins of about 150,000 daltons, composed of two identical light chains (LCs) and two identical heavy chains (HCs). Each light chain is linked to a heavy chain by one covalent disulfide bond, while the number of disulfide linkages varies between the heavy chains of different immunoglobulin isotypes. Each heavy and light chain also has regularly spaced intrachain disulfide bridges between cysteines. Each heavy chain has at a variable domain, followed by a number of constant domains. The variable domains are disposed closer to the amino-terminal (N-terminal) portion of the HC than are the constant domains; conversely, the constant domains are disposed closer to the carboxy-terminal (C-terminal) portion of the HC than are the variable domains. Similarly, each light chain has a variable domain at one end (towards the N-terminal) and a constant domain at its other end (towards the C-terminal); the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)). The variable domains form the antigen-binding sites; thus an intact antibody has two antigen binding sites composed of variable domains of the LC and HC pairs.

"Antibody fragment", and all grammatical variants thereof, as used herein are defined as a (1) portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody, and (2) constructs comprising a portion of an intact antibody (as defined by the amino acid sequence of the intact antibody) comprising the antigen binding site or variable region of the intact antibody. Examples of antibody fragments include Fab, Fab', Fab'-SH, F(ab')2, Fd, Fc, Fv, diabodies, and any other "Non-single-chain antigen-binding unit" as described, e.g., in U.S. Pat. No. 7,429,652. The term "intact antibody" refers to the complete antibody, or the amino acid sequence of the complete antibody, of which an antibody fragment is a part. It will be understood that an antibody fragment may be produced by partial digestion (e.g., by papain or pepsin) of an intact antibody, or may be produced by recombinant or other means.

As used herein, a "labeled antibody" refers to an antibody (whether intact or an antibody fragment) which is detectable by way of a label attached to the antibody. Such a label may be covalently attached to the antibody; such a label may be a dye, a radioisotope, a recognizable epitope (e.g., an epitope tag), or other label. A labeled antibody may include one, or may include multiple labels; multiple labels may be homogeneous or may be heterogeneous (e.g., a labeled antibody may have a plurality of fluorescent moieties covalently linked to the antibody (homogeneous) or may have a fluorescent moiety and a radioactive moiety linked to the antibody (heterogeneous)).

As used herein, the term "substantial" means more than a minimal or insignificant amount; and "substantially" means more than a minimally or insignificantly. Thus, for example, the phrase "substantially the same", as used herein, denotes a sufficiently high degree of similarity between two numeric values such that one of skill in the art would consider the similarity between the two values to be of statistical significance within the context of the characteristic measured by said values. Thus, two values that are substantially the same as each other is typically less than about 20%, and may be less than about 10%, preferably less than about 5%, and may be less than about 4%, as a function of the reference value or comparator value.

As used herein, the terms "equivalently diluted", "equivalent dilution", and the like refer to two or more diluted solutions, for which the ratio of the original volume to the final volume of the first solution is the same as the ratio of the original volume to the final volume of the second (and subsequent) solution or solutions. Thus, two solutions which are equivalently diluted are each diluted by the same ratio (as compared to the original solution volume); such solutions may be described as having been diluted by same dilution factor. For example, where a 100 μL sample is diluted to provide 1 mL of diluted sample (i.e., diluted by a factor of 10), an equivalently diluted calibrator is a calibrator that is diluted by a factor of 10 (e.g., a 1 mL calibrator solution that is diluted to provide 10 mL of diluted calibrator).

As used herein, the term "biological sample" refers to a fluid, tissue, or other material collected from a subject. Examples of biological samples can include but are not limited to, blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk and/or other excretions. Biological samples may include nasopharyngeal wash, or other fluid obtained by washing a body cavity or surface of a subject, or by washing a swab following application of the swab to a body cavity or surface of a subject. Nasal swabs, throat swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone. The sample may be provided from a human or animal. The sample may be provided from a mammal, vertebrate, such as murines, simians, humans, farm animals, sport animals, or pets. The sample may be collected from a living or dead subject. The sample may be collected fresh from a subject or may have undergone some form of pre-processing, storage, or transport.

A sample may be, for example, a bodily fluid sample obtained from a subject. The sample may be an aqueous or gaseous sample. The sample may be a gel. The sample may include one or more fluid component. In some instances, solid or semi-solid samples may be provided. The sample may include tissue collected from the subject. The sample may include a bodily fluid, secretion, and/or tissue of a subject. The sample may be a biological sample. The biological sample may be a clinical sample. The biological sample may be a bodily fluid, a secretion, and/or a tissue sample. Examples of biological samples may include but are not limited to, whole blood, blood serum, blood plasma, saliva, urine, gastric fluid, digestive fluid, tears, stool, semen, vaginal fluid, interstitial fluid, fluid derived from tumorous tissue, ocular fluids, sweat, mucus, earwax, oil, glandular secretions, breath, spinal fluid, hair, fingernails, skin cells, throat swab, nasal swab, nasopharyngeal wash, spinal fluid, cerebral spinal fluid, tissue, biopsy, placental fluid, amniotic fluid, cord blood, lymphatic fluid, fluid from a body cavity, sputum, pus, microbiota, meconium, breast milk, and other secretions and excretions.

A sample may be provided by a human or animal. A sample may be provided by a vertebrate animal; such a vertebrate animal may be a mammal. A sample may be provided by a mammal selected from the groups of mammals consisting of murine, ovine, bovine, equine, canine, simian, human, and other mammals. A sample may be provided by a farm animal, a sport animal, or a pet. The sample may be collected from a living or dead subject.

As used herein, a sample may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume may be defined as defined above. A blood sample may be diluted prior to analysis; a portion of a blood sample may be diluted prior to analysis; a portion of a blood sample may be an aliquot of untreated (e.g., whole blood), or may be an aliquot of blood plasma, or may be an aliquot of blood serum, or may be an aliquot of another portion or component of blood.

A sample may be a small-volume sample, or no more than a small-volume portion of a sample, where a small volume comprises a volume as defined above. A sample, or a portion thereof, may be diluted after collection. A sample, or a portion thereof, may be diluted prior to analysis. A sample, or a portion thereof, may be diluted prior to detection, quantification, characterization, or measurement of an analyte in the sample, or a portion thereof.

One or more collection mechanisms may be used in the collection of a sample from a subject. A collection mechanism may use one or more principle in collecting the sample. For example, a sample collection mechanism may use gravity, capillary action, surface tension, aspiration, vacuum force, pressure differential, density differential, thermal differential, or any other mechanism in collecting the sample, or a combination thereof. A bodily fluid may be drawn from a subject and provided to a device in a variety of ways, including but not limited to, finger-stick, lancing, injection, pumping, swabbing, pipetting, breathing, and/or any other technique described elsewhere herein. The bodily fluid may be provided using a bodily fluid collector. A bodily fluid collector may include a lancet, capillary, tube, pipette, syringe, needle, microneedle, pump, porous membrane or any other collector.

In one embodiment, a lancet punctures the skin of a subject and draws a sample using, for example, gravity, capillary action, aspiration, pressure differential and/or vacuum force. In some embodiments, a patch may comprise a plurality of microneedles, which may puncture the skin of a subject. Where needed, the lancet, the patch, or any other bodily fluid collector may be activated by a variety of mechanical, electrical, electromechanical, or any other known activation mechanism or any combination of such methods.

In one example, a subject's finger (or other portion of the subject's body) may be punctured to yield a bodily fluid. The bodily fluid may be collected using a capillary tube, pipette, swab, drop, or any other mechanism known in the art. In another embodiment where no active mechanism (beyond the body) is required, a subject can simply provide a bodily fluid to the device, as for example, could occur with a saliva sample or a finger-stick sample.

A bodily fluid may be drawn from a subject and provided to a device in a variety of ways, including but not limited to, finger-stick, lancing, injection, and/or pipetting. The bodily fluid may be collected using venous or non-venous methods. The bodily fluid may be provided using a bodily fluid collector. A bodily fluid collector may include a lancet, capillary, tube, pipette, syringe, venous draw, or any other collector described elsewhere herein. In one embodiment, a lancet punctures the skin and draws a sample using, for example, gravity, capillary action, aspiration, or vacuum force. The lancet may be part of the reader device, part of the cartridge, part of a system, or a stand-alone component, which can be disposable. Where needed, the lancet may be activated by a variety of mechanical, electrical, electromechanical, or any other known activation mechanism or any combination of such methods. In one example, a subject's finger (or other portion of the subject's body) may be punctured to yield a bodily fluid. Examples of other portions of the subject's body may include, but is not limited to, the subject's hand, wrist, aim, torso, leg, foot, ear, or neck. The bodily fluid may be collected using a capillary tube, pipette, or any other mechanism known in the art. The capillary tube or pipette may be separate from the device and/or cartridge, or may be a part of a device and/or cartridge or vessel. In another embodiment where no active mechanism is required, a subject can simply provide a bodily fluid to the device or system, as for example, can occur with a saliva sample. The collected fluid can be placed within the device or system. A bodily fluid collector may be attached to the device or system, removably attachable to the device or system, or may be provided separately from the device or system.

As used herein, a "finger-stick" refers to: i) the act of making a small puncture in the skin of a subject, allowing a small amount (e.g., a droplet, or one, two, or a few drops) of blood to flow and become available for collection; ii) the puncture itself; and iii) the blood collected thereby. Blood may be liberated in a finger-stick, for example, by use of a lancet or other sharp implement effective to pierce the skin of a subject. Typically, only a small amount of blood is collected in this way.

When referring to a volume, e.g., a "finger-stick volume" or "the volume of a finger-stick", the term "finger-stick" refers to the volume of a few droplets of blood typically obtained from a finger-stick. A single droplet of blood may have a volume of about 20-50 µL, e.g., about 40 µL. Thus, a few droplets of blood obtained from a finger-stick may provide a volume of about 50 µL to about 250 µL, or about 75 µL to about 200 µL, or, in some instances, between about 100-150 µL. Advantages of obtaining blood from a finger-stick include minimal discomfort to the subject and ease of access, as compared to obtaining blood from a vein or artery. Typically, only a small amount of blood is collected in this way (e.g., the amount of blood collected from a finger-stick may be about 250 µL or less, or about 200 µL or less, or about 150 µL or less, or about 100 µL or less, or about 50 µL or less, or about 25 µL or less, or about 15 µL or less, or about 10 µL or less, or about 5 µL or less, or about 3 µL or less, or about 2 µL or less, or about 1 µL or less). Blood from a finger-stick may be collected, e.g., by needle, syringe, capillary tube, or other method. Blood from a finger-stick may be collected for transport to another location; for storage prior to use or analysis; for immediate use; or for a combination of the same.

In some embodiments of the assays and methods disclosed herein, measurements may be made using a small-volume sample, where a small volume comprises about 500

µL or less, or about 400 µL or less, or about 300 µL or less, or about 250 µL or less, or about 200 µL or less, or about 150 µL or less, or about 100 µL or less, or about 75 µL or less, or about 50 µL or less, or about 25 µL or less, or about 20 µL or less, or about 15 µL or less, or about 10 µL or less, or about 8 µL or less, or about 6 µL or less, or about 5 µL or less, or about 4 µL or less, or about 3 µL or less, or about 2 µL or less, or about 1 µL or less, or about 0.5 µL or less, or about 0.4 µL or less, or about 0.3 µL or less, or about 0.2 µL or less, or about 0.1 µL or less. In embodiments, a small-volume sample comprises a small volume of no more than about 0.05 µL; or comprises no more than about 0.01 µL.

Assay methods disclosed herein may be performed on automatic sample analysis devices and systems, including commercially available automatic sample analysis devices and systems. Commercially available automatic sample analysis devices and systems may be obtained, for example, from Abbott (Abbott Diagnostics, Lake Forest, Ill., USA), Roche (Roche Diagnostics, Basel, CH), Siemens (Siemens Healthcare Diagnostics, Malvern, Pa., USA), Beckman Coulter (Beckman Coulter, Inc., Brea, Calif., USA), Ortho Clinical Diagnostics (Ortho Clinical Diagnostics, Rochester, N.Y., USA), and other manufacturers. Some analysis devices and systems are described in the scientific literature, in some patents, and some analyzers are commercially available. Current commercial analyzers include, for example, the DiaSorin Analyzers (DiaSorin S. p. A., Saluggia, Italy); the ADVIA Chemical Systems (Siemens Healthcare Diagnostics, Malvern, Pa., USA); the BD Max™ (Becton Dickinson, Franklin Lakes, N.J., USA); the ThunderBolt® from Gold Standard Diagnostics (Davis, Calif., USA); Cobas® Analyzers (Roche Diagnostics, Basel, CH); Ventana Symphony systems (Ventana Medical Systems, a division of Roche); the Bloodhound™ system of analyzers (Constitution Medical Investors, Inc., now a subsidiary of Roche); the CELL-DYN Ruby system (Abbott Diagnostics, Lake Forest, Ill., USA); and others.

An automatic sample analysis device or system may be configured to receive the sample, whether it be directly from a subject, from a bodily fluid collector, or from any other mechanism. A sample may be placed within an automatic sample analysis device or system. A sample collection unit of the device may be configured to receive the sample. In some embodiments, a sample may be provided directly to an automatic sample analysis device or system, or a vessel or component may be used as a conduit or means for providing a sample to an automatic sample analysis device or system.

In embodiments, devices and systems may be modified for use with small-volume samples. For example, clinical analysis devices and systems having sample vessels designed for samples having volumes most readily measured in milliliters (mL) (e.g., requiring minimum volumes of about 1 mL or more) may be modified for use with small-volume samples (e.g., samples having volumes most readily measured in microliters (µL)) by placing inserts into the sample vessels, effective that the volume available for the sample is reduced while the outer dimensions of the sample vessels remain unchanged, and so remain compatible with the clinical analysis devices or systems. Thus, in such embodiments, a modified sample container may be used in a clinical analysis device, where the modification comprises placing an insert into the sample container effective to reduce the space available for the sample. In embodiments, methods for modifying the analysis of samples in a clinical analysis device include reducing the sample volume that is analyzed by the clinical analysis device by placing an insert into the sample container. In embodiments, methods for modifying the analysis of samples in a clinical analysis device include reducing the sample volume that is analyzed by the clinical analysis device by providing a substitute or replacement sample container having a smaller volume than the original sample container.

In embodiments, methods for reducing the volume of sample used during, or required for, sample analysis include providing an insert which fits in a sample container effective to reduce the volume of sample held by the combined sample container and insert; or providing a substitute or replacement sample container which has a smaller volume than the original sample container. The sample may be contained within a sample container during at least a portion of the performance of said original assay, said sample container comprising an internal cavity for holding said sample, said internal cavity having a volume, and wherein any of the foregoing methods comprise reducing said volume of said internal cavity. In embodiments, reducing the volume of said internal cavity comprises providing an alternative sample container.

In embodiments, reducing the volume of said internal cavity comprises placing an insert into said internal cavity. In embodiments, an insert may comprise an insert cavity configured to hold said sample, wherein said insert cavity comprises a volume less than said internal cavity volume. The sample held in an insert may be a diluted sample, or may be an undiluted sample. Thus, in embodiments, an insert is effective to insure that the residual amount of sample remaining in a sample container (after draining the container) comprises only a small volume of sample. In embodiments, an insert may be configured effective to reduce the amount of residual sample volume remaining in the insert in a sample container after draining the insert in the sample container, as compared to the amount of residual sample volume that would remain after draining sample from the sample container in the absence of the insert. In embodiments, an insert may be configured effective that optical signals indicative of the presence of, or quantification of, a target substance in a sample contained within said insert may be detected by said optical detector.

As disclosed herein, a sample or sample aliquot may be diluted; a first sample aliquot (or sample) may be diluted by a first dilution factor that is different than the dilution factor by which a second sample aliquot is diluted, and a first sample may be diluted by a different amount than a second sample aliquot (or sample). In embodiments, a first sample aliquot (or sample) may be diluted and a second sample aliquot (or sample) may not be diluted.

In embodiments, a sample may be diluted by operation of an automatic sample analysis device or system, and then a target analyte in the sample is reacted or labeled, and the presence or absence of the target analyte is detected, or the amount or level of target analyte in the sample is measured. Following such detection and/or measurement, a signal or other indication regarding the presence or absence, or level, or both, of the target analyte in the sample is provided.

In embodiments, a reagent may be, or may be used as, a diluent, and, in embodiments, may be used to dilute a sample. In embodiments, a diluent and a sample may be mixed within an automatic sample analysis device or system. In embodiments, a diluent and a sample may be mixed within an automatic sample analysis device or system, and the diluted sample may further be mixed with a reagent. In embodiments, a diluent, a sample, and a reagent may be mixed within an automatic sample analysis device or system.

In embodiments, a calibration reagent may be diluted within an automatic sample analysis device or system, or within the housing thereof. In embodiments, a plurality of calibrators may be diluted within an automatic sample analysis device or system, or within the housing thereof. In embodiments, a sample provided on a cartridge may be diluted within an automatic sample analysis device or system, or within the housing thereof, and one or more calibration reagents may be diluted within the automatic sample analysis device or system, or within the housing thereof.

In embodiments, a sample may be diluted prior to delivery of the cartridge to an automatic sample analysis device or system, and one or more calibration reagents (i.e., one or more calibrators) may be diluted prior to delivery of the sample or of the calibrator to an automatic sample analysis device or system.

In embodiments, a sample or sample aliquot may be diluted; a first sample aliquot (or sample) may be diluted by a first dilution factor that is different than the dilution factor by which a second sample aliquot is diluted, and a first sample may be diluted by a different amount than a second sample aliquot (or sample). In embodiments, a first sample aliquot (or sample) may be diluted and a second sample aliquot (or sample) may not be diluted.

Sample Analysis

In one non-limiting example, some goals of sample analysis include detecting the presence or absence of a target analyte in a sample, and determining the amount of a target analyte in a sample. Assays for detecting the presence or absence of a target analyte in a sample, and assays for determining the amount of a target analyte in a sample are examples of methods of sample analysis. Performance of sample analysis includes processing a sample, and includes analyzing a sample. Thus, sample analysis includes processing steps and includes analyzing steps. It will be understood that sample analysis may be performed on a portion of a sample as well as on an entire sample. It will be understood that sample analysis may be performed on a diluted sample, or portion thereof, as well as on an undiluted sample, or portion thereof.

Methods, devices and systems for sample analysis may be used to perform assays on a sample, or samples, in order to detect, determine, or quantify some characteristic of a sample (such as detecting whether or not the sample contains a particular analyte, or such as determining the concentration of a particular analyte present in the sample). In an assay, a sample may be prepared for use, and may be used, in the assay in ways determined by the nature of the target analyte and by the nature and amount of sample available for use in the assay. Steps useful in preparing a sample for use in an assay may be termed "processing" steps, while steps which make, or are closely linked to making, measurements regarding the presence, or amount, or concentration of a target analyte may be termed "analyzing" steps.

Thus, sample analysis includes both processing step(s) and analyzing step(s).

Sample analysis includes processing of a sample, or portion thereof, whether diluted on undiluted. Processing may include, for non-limiting example, providing, storing, transporting, warming, cooling, freezing, filtering, coagulating, separating, centrifuging, diluting, preserving, and other steps.

Sample analysis also includes analyzing a sample, or portion thereof, whether diluted on undiluted. Analyzing may include, for non-limiting example, reacting, hybridizing, binding, illuminating, detecting, comparing (e.g., to a standard curve), subtracting (e.g., values obtained from a blank), and other steps.

Some steps, such as mixing, sonicating, labeling, incubating, chelating, and other steps, may be considered processing steps, or may be considered analyzing steps, or both.

Typical assays of biological materials may require many milliliters of sample. In many cases where different assays are to be run, e.g., for multiple analytes, or for different analyte types, multiple samples may be obtained. Such volumes of sample, and such multiple acquisitions of sample from a subject, may be difficult, uncomfortable, and time-consuming.

However, reducing the volume of sample that is required for sample analysis provides advantages in comfort, accessibility, and cost; and may provide advantages in speed, simplicity and ease of analysis. Increasing the speed of an assay provides quicker results, which will typically be appreciated by the subject from whom the sample is taken.

Current commercial analyzers typically add sample to a vessel (such as a cuvette) for placement in an analysis device or system. Reagents may be added to the sample, including, for example, reagents containing molecules which specifically bind to or react with a target substance, or analyte, in the sample. Further reagents may be added which label, or allow visualization or detection of, the target substance. The presence of the substance, or the amount of the substance, in the sample may be detected or measured. The detection or measurement may be compared to a calibration curve. Finally, the results of these actions may be printed out or otherwise communicated to a user.

As disclosed herein, it is advantageous to reduce the volume of sample required for testing. For example, it is advantageous to reduce the volume of sample used in, or required for, processing steps; and it is advantageous to reduce the volume of sample used in, or required for, analyzing steps. However, simply providing smaller amounts of sample to a machine, or using smaller amounts of sample in an assay, without further modifications, is typically fruitless, since the volumes of reagents; the concentrations of reagents and of constituents of reagents; the fluid-handling apparatus (where the sample is liquid); the transport means (for solid or fluid samples); the illumination means (if any); the signal detection apparatus; and other means, mechanisms, devices, systems, and system particulars may be incorrect, mis-matched, or incompatible with the reduced volume samples.

It is also advantageous to reduce the time required to perform a test. However, reducing the volume of a sample taken from a subject will reduce the amount of target substance in the sample, and will typically reduce the signal produced by assays for the detection or quantification of the substance, all of which may lead to an increase in the time require to perform a test.

Methods for Diluting a Sample and for Using a Diluted Sample

An automatic sample analysis device or system may be configured to accept a sample, or aliquot of a sample, and to analyze the sample for the presence or absence of an analyte, or of a plurality of analytes. In embodiments, an automatic sample analysis device or system may analyze a sample, or a calibration reagent, or both. A sample, or aliquot thereof, may be diluted when provided to an automatic sample analysis device or system. A sample, or aliquot thereof, may be provided undiluted to an automatic sample analysis device or system. A sample, or aliquot thereof, may be diluted by an automatic sample analysis device or system. A calibration reagent may be provided undiluted to an automatic sample analysis device or system, or may be diluted when provided to an automatic sample analysis device or system. A calibration reagent may be diluted by an automatic sample analysis device or system.

Dilution of a small-volume sample, or a small-volume aliquot of a sample, increases the volume of the material subsequently available for analysis following dilution, although dilution also decreases the concentration of analytes in the resulting diluted solution. The resulting greater volume following dilution may make transport, manipulation, mixing, aliquotting, further dilution, or other action performed with or on the resulting diluted sample easier to perform than would be the case in the absence of such dilution. Accordingly, dilution of a sample, or a small-volume aliquot of a sample, may provide advantages for the analysis of the sample or sample aliquot.

In embodiments, the presence or absence of a target analyte in the diluted sample is detected within an automatic sample analysis device or system. In embodiments, the presence or absence of two target analytes in one or more portions of a diluted sample are detected within an automatic sample analysis device or system. In embodiments, the amount of a target analyte in the diluted sample is measured within an automatic sample analysis device or system. In embodiments, the amounts of two target analytes in one or more portions of a diluted sample are measured within an automatic sample analysis device or system. In embodiments, the presence or absence, or the amount, of a first target analyte in a sample or portion of a sample, is detected or measured within an automatic sample analysis device or system, and the presence or absence, or the amount, of a second target analyte in a sample or portion of a sample, is detected or measured within the same automatic sample analysis device or system. In embodiments, the presence or absence, or amounts, of two or more target analytes in one or more portions of a sample, one or more of which may be diluted samples or diluted sample portions, are detected within one automatic sample analysis device or system.

In embodiments, the presence or absence, or amount, of a target analyte in a sample, or portion of a sample, is detected or measured by optical means within an automatic sample analysis device or system. In embodiments, the presence or absence, or amount, of a target analyte in a diluted sample, or a diluted sample portion, is detected or measured by optical means within an automatic sample analysis device or system. In embodiments, the presence or absence, or the amounts, of two or more target analytes in a sample, sample portion, diluted sample, or a diluted sample portion, are detected or measured by optical means within an automatic sample analysis device or system. In embodiments, optical detection means may include spectrophotometers, photomultiplier tubes, charge-coupled devices, photodiodes, avalanche photodiodes, avalanche photodiode arrays, pin diodes, digital cameras, and other optical devices and optical detection means.

Applicant provides herein methods for reducing the volume of sample required for assays for detecting the presence of a target substance in a sample. Applicant provides herein methods for reducing the time required for the performance of assays for detecting the presence of a target substance in a sample. Applicant provides herein methods for reducing the volume of sample required, and for reducing the time required, for the performance of assays for detecting the presence of a target substance in a sample.

Applicant provides herein methods for reducing the volume of sample used for, or required for, processing steps in sample analysis. Applicant provides herein methods for reducing the volume of sample used for, or required for, analyzing steps in sample analysis. Applicant provides herein methods for reducing the volume of sample used for, or required for, both processing steps and analyzing steps in sample analysis.

Applicant provides herein methods for reducing the volume of sample required for assays for quantifying the amount of a target substance in a sample. Applicant provides herein methods for reducing the time required for the performance of assays for quantifying the amount of a target substance in a sample. Applicant provides herein methods for reducing the volume of sample required and for reducing the time required for the performance of assays for quantifying the amount of a target substance in a sample.

In embodiments, the methods comprise a step of diluting a sample. Such dilution steps are typically performed prior to other assay steps. In embodiments, the methods comprise a step of diluting a sample and of diluting a calibrator (e.g., a reagent containing a known amount of analyte that is used as a reference standard). For example, methods may comprise a step of diluting a sample by a dilution factor and of diluting a calibrator by the same dilution factor. Methods may further comprise a step of diluting a sample by a dilution factor and of diluting a calibrator by the same dilution factor. Such dilution steps are typically performed prior to other assay steps. In embodiments, reagents used in such assays are prepared in conformance with the dilution factor, e.g., the reagent concentrations and reaction times of the assay are configured for use with samples (and calibrators) that have been diluted by the dilution factor.

In embodiments, the methods comprise a step of diluting a sample, e.g., diluting a sample prior to mixing the sample with a reagent, prior to detecting an analyte in the sample, or prior to other treatment steps. In embodiments, such a further step of diluting a sample is performed prior to all steps of standard protocols, or of manufacturer protocols, for the analysis of the sample. In embodiments, such a further step of diluting a sample is performed prior to a pre-treatment step, and prior to treatment steps in the analysis of the sample. In embodiments, such a further step of diluting a sample is performed following a pre-treatment step, and prior to treatment steps in the analysis of the sample. In embodiments, such a further step of diluting a sample is performed prior to all other steps in the analysis of the sample.

Dilution of a sample, or aliquot thereof, by a factor of "X" means that the resulting total volume, following addition of diluent to a sample (or aliquot thereof), is "X" times the volume of the original sample volume (or aliquot volume). Dilution of a sample, or aliquot thereof, by a factor of X results in a dilution ratio of X:1. Accordingly, dilution of a sample, or aliquot thereof, by a factor of 2 means that the resulting total volume, following addition of diluent to a sample (or aliquot thereof), is twice the volume of the original sample volume (or aliquot volume). Dilution of a sample, or aliquot thereof, by a factor of 2 results in a dilution ratio of 2:1. Accordingly, dilution of a sample, or aliquot thereof, by a factor of 3 results in a dilution ratio of 3:1; dilution by a factor of 4 results in a dilution ratio of 4:1; dilution by a factor of 10 results in a dilution ratio of 10:1; and similarly for other dilution factors.

In embodiments, methods for detecting the presence or absence of, or for measuring a level of, an analyte in a diluted sample, where the sample has been diluted by a dilution factor, include further steps comprising measuring the amount of analyte in a calibration solution that has been prepared to have an amount of analyte that is proportional to the amount of analyte contained in a calibration solution that has been diluted by the same dilution factor as the sample (i.e., the sample and the calibration solution are equivalently diluted).

In embodiments, a sample may be diluted by a factor of 2, 3, 4, 5, 6, 7, 8, 9, 10, 12, 14, 15, 16, 18, 20, 25, 30, 35, 40, 50, 100, or more. In embodiments, a sample may be diluted by a factor of 2, 3, 4, 5, 6, 7, 8, 9, 10, 12, 14, 15, 16, 18, 20, 25, 30, 35, 40, 50, 75, 100, 150, 200, 250, 500, 1000, or more after a pre-treatment step, and prior to other steps in the analysis of a sample. In embodiments, a sample may be diluted by a factor of 2, 3, 4, 5, 6, 7, 8, 9, 10, 12, 14, 15, 16, 18, 20, 25, 30, 35, 40, 50, 75, 100, 150, 200, 250, 500, 1000, or more prior to all other steps in the analysis of a sample. In embodiments, a sample may be diluted by a factor of 2, 3, 4, 5, 6, 7, 8, 9, 10, 12, 14, 15, 16, 18, 20, 25, 30, 35, 40, 50, 75, 100, 150, 200, 250, 500, 1000, or more during the analysis of a sample, wherein the analysis is directed at detecting the presence or amount of at least two target analytes in the sample; in further embodiments, the analysis of the sample is directed at detecting the presence or amount of at least three target analytes in the sample. In embodiments, more than one aliquot of the sample, or more than one aliquot of the diluted sample, is used in detecting the presence or amount of an analyte, or of a plurality of analytes.

In embodiments, methods comprising a step of diluting a sample also include a step of analyzing a calibrator; in embodiments, the calibrator is diluted, e.g., by the same dilution factor as the sample. In embodiments, a step of diluting a sample and a step of diluting a calibrator are performed at substantially the same time. In embodiments, a calibrator may be diluted by a factor of 2, 3, 4, 5, 6, 7, 8, 9, 10, 12, 14, 15, 16, 18, 20, 25, 30, 35, 40, 50, 75, 100, 150, 200, 250, 500, 1000, or more.

A portion of a sample, such as a portion of a small sample, may be a diluted portion. For example, a portion of a sample may be divided from an original undivided sample, and then that portion may be diluted (e.g., by mixing with a diluent, or by placement of the sample portion into a diluent). In embodiments, a diluted portion of a sample may be provided by diluting an original undivided sample (e.g., by mixing with a diluent to the original undivided sample, or by placement of the original undivided sample into a diluent), and then taking a portion of the diluted sample to provide a diluted sample portion. In embodiments, a diluted portion of a sample may be provided by taking a portion of a diluted sample or a diluted sample portion, and further diluting that portion.

Applicant discloses methods for detecting the presence or absence, or measuring a level, of an analyte in a sample using an automatic sample analysis device or system in the performance of an assay protocol, the method comprising:

Diluting said sample by mixing with a diluent;

Reacting or labeling a target analyte in said diluted sample after said dilution step, wherein said reacting or labeling is performed within an automatic sample analysis device or system;

Detecting said reaction or said label in said diluted sample after said reacting or labeling step, wherein said detecting is performed within an automatic sample analysis device or system;

Transmitting a signal communicating the results of said assay protocol;

Whereby the presence or absence of, or level of, the analyte is detected or measured in said sample by use of said automatic sample analysis device or system in the performance of said assay protocol. In embodiments, the automatic sample analysis device or system is located at, or near the premises of a retail location, such as, e.g., a market, a retail pharmacy, a hospital, medical clinic, dialysis center, doctor's office, dentist's office, or other medically related location.

In embodiments, the method comprises detection of the analyte in a sample according to an assay protocol that differs from the manufacturer's suggested assay protocols, or other standard protocols, by inclusion of a dilution step. In embodiments, the sample is diluted prior to the performance of an assay comprising the steps of a manufacturer's suggested assay protocol, or other standard protocols, for the automatic sample analysis device or system.

Further embodiments of methods for detecting the presence or absence, or measuring a level, of an analyte in a sample using an automatic sample analysis device or system comprise:

Diluting said sample by mixing with a diluent;

Mixing a first reagent with said diluted sample at a first mixing time;

Mixing a second reagent with said mixture comprising diluted sample and said first reagent at a second mixing time;

Detecting the presence or absence, or measuring a level, of said analyte at a first detection time using said detector; and Transmitting a signal communicating the results of said assay protocol;

Whereby the presence or absence of, or level of, the analyte is detected or measured in said sample. In further embodiments, Applicant discloses a method for detecting the presence or absence, or measuring a level, of at least two analytes in a single sample using an automatic sample analysis device or system comprising a detector in the performance of an assay protocol, said at least two analytes comprising a first analyte and a second analyte, the method comprising:

Diluting said sample by mixing with a diluent;

Dividing said diluted sample into at least two aliquots comprising at least a first aliquot and a second aliquot of the diluted sample, wherein said at least two aliquots are isolated from each other and are held within at least two containers within said automatic sample analysis device or system;

Mixing a first reagent with said first aliquot of the diluted sample at a first mixing time;

Mixing a second reagent with said second aliquot of the mixture comprising diluted sample and said second reagent at a second mixing time;

Detecting the presence or absence, or measuring a level, of said first analyte at a first detection time using said detector;

Detecting the presence or absence, or measuring a level, of said second analyte at a second detection time using the detector; and Transmitting a signal communicating the results of said assay protocol;

Whereby the presence or absence, or levels, of at least two analytes are detected or measured in said sample by use of said automatic sample analysis device or system. In embodiments, the first mixing time is different than the second mixing time. In embodiments, the first detection time is different than the second detection time.

Further embodiments include the following methods.

A method for detecting the presence or absence, or measuring a level, of at least two analytes in a single sample using an automatic sample analysis device or system comprising a detector, said at least two analytes comprising a first analyte and a second analyte, the method comprising:

Diluting said sample by mixing with a diluent;

Dividing said diluted sample into at least two aliquots comprising at least a first aliquot and a second aliquot of the diluted sample, wherein said at least two aliquots are isolated from each other and are held within at least two containers within said automatic sample analysis device or system;

Mixing a first reagent with said first aliquot of the diluted sample at a first mixing time, wherein said mixing comprises transporting said first reagent or said first aliquot along one or more linear paths within the automatic sample analysis device or system;

Mixing a second reagent with said second aliquot of the diluted sample at a second mixing time, wherein said mixing comprises transporting said second reagent or said second aliquot along one or more linear paths within the automatic sample analysis device or system;

Detecting the presence or absence, or measuring a level, of said first analyte at a first detection time using said detector;

Detecting the presence or absence, or measuring a level, of said second analyte at a second detection time using the detector; and Transmitting a signal communicating the results of said assay protocol;

Whereby the presence or absence of, or level of, of at least two analytes are detected or measured in a sample by use of said automatic sample analysis device or system. In embodiments, the first mixing time is different than the second mixing time. In embodiments, the first detection time is different than the second detection time. In embodiments, the presence or absence, or levels, of at least two analytes are detected or measured in a sample using an automatic sample analysis device or system within a short period of time. In embodiments, the short period of time is selected from one hour, 50 minutes, 40 minutes, 30 minutes, 20 minutes, 10 minutes, and 5 minutes.

In embodiments of the methods disclosed herein, detecting the presence or absence of, or measuring a level of, an analyte comprises comparing i) a signal produced by a detector from a detector measurement of a diluted sample with ii) a signal produced by a detector from a detector measurement of a diluted calibration solution, wherein the dilution of the calibration solution is equivalent to the dilution of the diluted sample.

In embodiments of the methods disclosed herein, detecting the presence or absence of, or measuring a level of, an analyte comprises comparing i) a signal produced by a detector from a detector measurement of a diluted sample with ii) a plurality of signals produced by a detector from a detector measurement of a plurality of diluted calibration solutions, wherein the dilution of the calibration solution is equivalent to the dilution of the diluted sample, wherein prior to said dilution, the plurality of calibration solutions contained a plurality of known concentrations of a target calibrator; in embodiments, said target calibrator comprises the analyte to be detected or measured in the sample.

In further embodiments, methods for detecting the presence or absence of, or for measuring a level of an analyte in a sample include i) a step comprising measuring a level of an analyte in a diluted sample or diluted sample aliquot and ii) a step comprising measuring the amount of analyte in a calibration solution that has been diluted by the same amount of dilution as the sample or sample aliquot. In embodiments, a sample and a calibration solution are each diluted by the same amount by an automatic operation. In embodiments, a sample and a calibration solution are each diluted by the same amount by the same automatic operation, or by automatic operations performed by the same device or system. In embodiments, a sample and a calibration solution are each diluted by the same amount at substantially the same time. In embodiments, a sample and a calibration solution are each diluted by the same amount a sample and a calibration solution are each diluted by the same amount by the same automatic operation, or by automatic operations performed by the same device or system, at substantially the same time. In embodiments, a sample and a calibration solution are each diluted by the same amount a sample and a calibration solution are each diluted by the same amount by the same automatic operation, or by automatic operations performed by the same device or system, by sequential operations including dilution of the sample and of the calibration solution, wherein the sample is diluted within a short period of time of the dilution of the calibration solution.

In embodiments, assays performed according to the methods disclosed herein comprise using an automatic sample analysis device or system in a manner that differs from the device or system manufacturer's protocol comprise assays in which a sample is diluted prior to the performance of assay steps of according to the device or system manufacturer's protocol, or other standard protocols for the device or system. In embodiments, assays performed according to the methods disclosed herein using an automatic sample analysis device or system in a manner that differs from the device or system manufacturer's protocol comprise assays in which a sample is diluted and a calibrator (e.g., a calibration reagent) is diluted prior to the performance of assay steps of according to the device or system manufacturer's protocol. In embodiments in which an assay performed according to the methods disclosed herein using an automatic sample analysis device or system is performed in a manner that differs from the device or system manufacturer's protocol, in which a sample and a calibrator are diluted prior to the performance of assay steps of according to the device or system manufacturer's protocol, the sample and the calibrator are equivalently diluted. A sample and a calibrator (e.g., a calibration solution containing a known concentration of an analyte) are equivalently diluted when the volume ratio of sample to diluted sample is the same as the volume ratio of calibrator to diluted calibrator. Thus, where a calibrator and a sample are equivalently diluted, the dilution of the calibrator is equivalent to the dilution of the diluted sample (the sample and the calibrator have been diluted by the same dilution factor).

In embodiments, each and any of the methods disclosed herein may be used to detect at least two analytes of different analyte types that are present in a single sample (such detection may be performed with the undivided sample, or with an aliquot of the sample, or with two or more aliquots of the sample). In embodiments, each and any of the methods disclosed herein may be used to detect at least two analytes of different analyte types from a small-volume biological sample within a short period of time (such detection may be performed with the undivided small-volume sample, or with an aliquot of the small-volume sample, or with two or more aliquots of the small-volume sample). In embodiments, methods disclosed herein may be used to detect at least three, or at least four, or at least five, or more analytes of different analyte types, all of which may be detected from a small biological sample (such detection may be performed with the undivided small-volume sample, or with an aliquot of the small-volume sample, or with two or more aliquots of the small-volume sample), and all of which may be detected within a short period of time. Analyte types which may be detected include nucleic acid analytes, protein analytes, lipid analytes, blood chemistry analytes (including chemical and ion concentrations), cell-surface markers, cell morphological markers, cytoplasmic markers, and other analyte types. Such methods may be performed by automatic sample analysis devices or systems according to the methods disclosed herein.

In embodiments, each and any of the methods disclosed herein may be used to detect at least two analytes of different analyte types that are present in a single sample (such detection may be performed with the undivided sample, or with an aliquot of the sample, or with two or more aliquots of the sample), and to further perform a cytometry assay on the sample or portion thereof. In embodiments, each and any of the methods disclosed herein may be used to detect at least two analytes of different analyte types from a small-volume biological sample within a short period of time (such detection may be performed with the undivided small-volume sample, or with an aliquot of the small-volume sample, or with two or more aliquots of the small-volume sample), and to further perform a cytometry assay on the sample or portion thereof. In embodiments, methods disclosed herein may be used to detect at least three, or at least four, or at least five, or more analytes of different analyte types, all of which may be detected from a small biological sample (such detection may be performed with the undivided small-volume sample, or with an aliquot of the small-volume sample, or with two or more aliquots of the small-volume sample), and all of which may be detected within a short period of time, and to further perform a cytometry assay on the sample or portion thereof. Analyte types which may be detected include nucleic acid analytes, protein analytes, lipid analytes, blood chemistry analytes (including chemical and ion concentrations), cell-surface markers, cell morphological markers, cytoplasmic markers, and other analyte types. Such methods may be performed by automatic sample analysis devices or systems according to the methods disclosed herein.

In embodiments, each and any of the methods disclosed herein may be used to detect an analyte, or at least two analytes, or more, present in a single sample, where the sample is a small sample (also termed a "small-volume sample"). For example, a small sample have a volume of about 500 µL or less, or about 400 µL or less, or about 300 µL or less, or about 250 µL or less, or about 200 µL or less, or about 150 µL or less, or about 100 µL or less, or about 75 µL or less, or about 50 µL or less, or about 25 µL or less, or about 20 µL or less, or about 15 µL or less, or about 10 µL or less, or about 8 µL or less, or about 6 µL or less, or about 5 µL or less, or about 4 µL or less, or about 3 µL or less, or about 2 µL or less, or about 1 µL or less, or about 0.5 µL or less, or about 0.4 µL or less, or about 0.3 µL or less, or about 0.2 µL or less, or about 0.1 µL or less. A small sample may be divided into aliquots or portions, where an aliquot or portion may have a volume of about 475 µL or less, or about 450 µL or less, or about 400 µL or less, or about 300 µL or less, or 250 µL or less, or about 200 µL or less, or about 150 µL or less, or about 100 µL or less, or about 75 µL or less, or about 50 µL or less, or about 25 µL or less, or about 20 µL or less, or about 15 µL or less, or about 10 µL or less, or about 8 µL or less, or about 6 µL or less, or about 5 µL or less, or about 4 µL or less, or about 3 µL or less, or about 2 µL or less, or about 1 µL or less, or about 0.5 µL or less, or about 0.4 µL or less, or about 0.3 µL or less, or about 0.2 µL or less, or about 0.1 µL or less.

A portion of a sample, such as a portion of a small sample, may be a diluted portion. For example, a portion of a sample may be divided from an original undivided sample, and then that portion may be diluted (e.g., by mixing with a diluent, or by placement of the sample portion into a diluent). In embodiments, a diluted portion of a sample may be provided by diluting an original undivided sample (e.g., by mixing with a diluent to the original undivided sample, or by placement of the original undivided sample into a diluent), and then taking a portion of the diluted sample to provide a diluted sample portion. In embodiments, a diluted portion of a sample may be provided by taking a portion of a diluted sample or a diluted sample portion, and further diluting that portion.

In embodiments, the methods disclosed herein may comprise detection, identification, measurement, and analysis of analytes and samples at room temperature, or at temperatures near 20° C. In embodiments, the methods disclosed herein may comprise detection, identification, measurement, and analysis of analytes and samples at elevated temperatures. In embodiments, elevated temperatures may be temperatures above about 25° C., above about 30° C., or above about 35° C. In embodiments, the methods disclosed herein may comprise detection, identification, measurement, and analysis of analytes and samples at temperatures of between about 32° C. and about 40° C. In embodiments, the methods disclosed herein may comprise detection, identification, measurement, and analysis of analytes and samples at temperatures of about 37° C.

In embodiments, each and any of the methods disclosed herein may be used to detect an analyte, or at least two analytes, or more, present in a single sample, may be performed by an automatic sample analysis device or system, where the methods are performed according to a protocol provided to the automatic sample analysis device or system, or are performed according to a protocol stored within the automatic sample analysis device or system.

In embodiments, protocols may be updated and may be tailored to one or more factors, where such factors may include characteristics of the automatic sample analysis device or system, or of its environment, or of materials used or incident to the analysis of a biological sample. For example, in embodiments, protocols may be updated and may be tailored to specific reagents and disposables, e.g., taking into account control reagents, calibrations of reagents, the specific properties and characteristics of reagents used in an assay.

In embodiments of each and any of the methods disclosed herein, a short period of time may comprise less than about an hour, or less than about 45 minutes, or less than about 30 minutes, or less than about 20 minutes, or less than about 10 minutes, or less than about 5 minutes, or less than about 4 minutes, or less than about 3 minutes, or less. In embodiments, a short period of time may begin when a sample is obtained from a subject. In embodiments, a short period of time may begin when a sample is provided to a sample analysis device or system. In embodiments, a short period of time may begin when a sample is provided to an automatic sample analysis device or system. In embodiments, a short period of time may begin when a sample is diluted. In embodiments, a short period of time may begin when a sample is diluted by a sample analysis device or system. In embodiments, a short period of time may begin when a sample is diluted by an automatic sample analysis device or system. In embodiments, a short period of time may begin when a sample is mixed with a reagent. In embodiments, a short period of time may begin when a sample is mixed with a reagent by a sample analysis device or system. In embodiments, a short period of time may begin when a sample is mixed with a reagent by an automatic sample analysis device or system.

In embodiments of each and any of the methods disclosed herein, an automatic sample analysis device or system may analyze a sample according to a protocol. In embodiments, an automatic sample analysis device or system may analyze a sample according to a fixed, pre-set protocol. In embodiments, an automatic sample analysis device or system may analyze a sample according to a protocol that may be prepared or altered for use with one or more of a particular type of subject, a particular type of sample, and a particular individual subject. In embodiments, an automatic sample analysis device or system may analyze a sample according to a protocol that may be updated or altered for use with a particular type of sample. In embodiments, an automatic sample analysis device or system may analyze a sample using a plurality of different reagents, wherein the different reagents of said plurality may be updated or altered for use with one or more of a particular of sample.

In embodiments of each and any of the methods disclosed herein, a sample may be delivered to an automatic sample analysis device or system; in embodiments, the sample delivered to an automatic sample analysis device or system is a diluted sample. In embodiments in which the sample is a diluted sample, the diluted sample may be mixed with a reagent within an automatic sample analysis device or system. In embodiments, such mixing with a reagent is performed prior to detection of the presence or absence of a target analyte in the diluted sample within an automatic sample analysis device or system.

In embodiments of each and any of the methods disclosed herein, the sample delivered to an automatic sample analysis device or system is an undiluted sample. In embodiments, an undiluted sample delivered to an automatic sample analysis device or system is diluted within an automatic sample analysis device or system. Such dilution within an automatic sample analysis device or system may be performed prior to analysis of the sample. In embodiments, the sample delivered to an automatic sample analysis device or system is an undiluted sample, and the sample is diluted and then mixed with a reagent prior to detection of the presence or absence of a target analyte in the diluted sample within an automatic sample analysis device or system.

In embodiments of each and any of the methods disclosed herein, including methods for detecting the presence or absence of, or measuring a level of, an analyte in a biological sample, may be performed on a blood sample. In embodiments, the blood sample comprises a blood sample collected by finger-stick. In embodiments, the blood sample comprises a blood sample collected by finger-stick, having a volume of less than about 250 µL of blood. In embodiments, the blood sample comprises a blood sample collected by finger-stick, having a volume of less than about 150 µL of blood. In embodiments, the blood sample comprises a blood sample collected by finger-stick, having a volume of less than about 100 µL of blood. In embodiments, the blood sample comprises a blood sample collected by finger-stick, having a volume of less than about 75 µL of blood. In embodiments, the blood sample comprises a blood sample collected by finger-stick, having a volume of less than about 50 µL of blood. In embodiments, the blood sample comprises a blood sample collected by finger-stick, having a volume of less than about 25 µL of blood. In embodiments, the blood sample comprises a blood sample collected by finger-stick, having a volume of less than about 10 µL of blood. In embodiments, the blood sample comprises a blood sample collected by finger-stick, having a volume of less than about 5 µL of blood. In embodiments, the blood sample comprises a blood sample collected by finger-stick, having a volume of less than about 1 µL of blood.

In embodiments of each and any of the methods disclosed herein, including methods for detecting the presence or absence of, or measuring a level of, an analyte in a biological sample, may be performed on a urine sample. In embodiments of each and any of the methods disclosed herein, including methods for detecting the presence or absence of, or measuring a level of, an analyte in a biological sample, may be performed on a saliva sample. In embodiments of each and any of the methods disclosed herein, including methods for detecting the presence or absence of, or measuring a level of, an analyte in a biological sample, may be performed on a sample selected from a throat swab, a nasal swab, and a nasopharyngeal wash.

In embodiments of each and any of the methods disclosed herein, including methods for detecting the presence or absence of, or measuring a level of, an analyte, methods may comprise detecting the presence or absence, or level of, at least two analytes in aliquots of a single sample, or at least three analytes in aliquots of a single sample, or at least four analytes in aliquots of a single sample.

In embodiments of each and any of the methods disclosed herein, including methods for detecting the presence or absence of, or measuring a level of, an analyte, methods may comprise detecting the presence or absence, or level of, at least one analyte and at least one cell type in aliquots of a single sample, or at least two analytes and at least one cell type in aliquots of a single sample, or at least three analytes and at least one cell type in aliquots of a single sample, or at least four analytes and at least one cell type in aliquots of a single sample.

In embodiments of each and any of the methods disclosed herein, including methods for detecting the presence or absence of, or measuring a level of, an analyte using an automatic sample analysis device or an automatic sample analysis system, such an automatic sample analysis device or an automatic sample analysis system may be modified for use with small-volume samples. Such modifications may include modification of a sample container, wherein said sample container is part of, or is used with, the automatic sample analysis device or automatic sample analysis system. Such modifications may include modification of a automatic sample analysis device or an automatic sample analysis system for use with small-volume samples by placement of an insert into a sample container, wherein said sample container is part of, or is used with, the automatic sample analysis device or automatic sample analysis system. Such modifications of automatic sample analysis devices or an automatic sample analysis systems, wherein the automatic sample analysis device or an automatic sample analysis system are configured for use with an original sample container having a first internal volume for holding a sample, may include providing or using a replacement sample container configured for use with small-volume samples, wherein said replacement sample container has a second internal volume for holding a sample, wherein said second internal volume of said replacement sample container is less than said first internal volume of said original sample container. Such modifications of automatic sample analysis devices or an automatic sample analysis systems, wherein the automatic sample analysis device or an automatic sample analysis system are configured for use with an original sample container having a first internal volume for holding a sample, may include providing or using a insert, comprising placing an insert into the original sample container effective to reduce the volume available to hold a sample, wherein said insert has a second internal volume for holding a sample, wherein said second internal volume of said insert is less than said first internal volume of said original sample container.

Further Methods for Reducing the Volume of Sample Required to Perform an Assay

Methods for reducing the volume of a sample, e.g., reducing the amount of sample required for an assay for the detection of, or quantification of, a target substance in a sample, include methods in which a sample container (such as, e.g., a cuvette, tube, caplet, or other container) is altered for use with smaller volumes of sample; such alterations include alterations in the volume of an internal chamber of a sample container (e.g., reduction in such volume), alterations in the shape of an internal chamber of a sample container (e.g., alterations making the chamber longer and narrower), alterations in a wall of an internal chamber of a sample container (e.g., providing a reflective, e.g., mirrored, or refractive (e.g., focusing) surface, and other alterations.

Methods for reducing the volume of a sample, e.g., reducing the amount of sample required for an assay for the detection of, or quantification of, a target substance in a sample, include methods in which an insert is provided and placed within a sample container (such as, e.g., a cuvette, tube, caplet, or other container), reducing the internal volume available to hold a sample. Such an insert may be configured to fit snugly within a cavity of a sample container, and to have a cavity for holding a sample, where the cavity of the insert has a smaller volume than the cavity of the sample container. Thus, methods for reducing the volume of a sample used for, or required for, processing steps in sample analysis include steps of placing such in insert within a sample container. In addition, methods for reducing the volume of a sample used for, or required for, analyzing steps in sample analysis include steps of placing such in insert within a sample container. Furthermore, methods for reducing the volume of a sample used for, or required for, processing steps and analyzing steps in sample analysis include steps of placing such in insert within a sample container.

Devices useful for reducing the volume of a sample, e.g., reducing the amount of sample required for an assay for the detection of, or quantification of, a target substance in a sample, include inserts configured for placement within a sample container having a sample container cavity (such as, e.g., a cuvette, tube, caplet, or other container), the insert having an internal cavity whose volume is less than the volume of the sample container cavity. Thus, such inserts are useful in reducing the volume of sample used for, or required for, processing steps in sample analysis; are useful in reducing the volume of sample used for, or required for, analyzing steps in sample analysis; and are useful in reducing the volume of sample used for, or required for, both processing steps and analyzing steps in sample analysis.

Methods for reducing the volume of a sample, e.g., reducing the amount of sample required for an assay for the detection of, or quantification of, a target substance in a sample, include methods in which a detector, such as a light detector, or an electronic detector, or other detector, is altered for use with smaller volumes of sample. Methods for reducing the volume of a sample, e.g., reducing the amount of sample required for an assay for the detection of, or quantification of, a target substance in a sample, include methods in which a sample container is altered for use with smaller volumes of sample, so that, for example, a long narrow chamber provides a suitable pathlength for optical detection while requiring a smaller sample volume than an original container. Methods for reducing the volume of a sample, e.g., reducing the amount of sample required for an assay for the detection of, or quantification of, a target substance in a sample, include methods in which a source of illumination required for optical detection or measurement is altered for use with smaller volumes of sample; typically, such alteration includes increasing illumination intensity, but may also, or instead, include altering the wavelength of light, or the polarization of light, provided by the source of illumination. Methods for reducing the volume of a sample, e.g., reducing the amount of sample required for an assay for the detection of, or quantification of, a target substance in a sample, include methods in which a sample is placed nearer to a detector, such as a light detector, or an electronic detector, or other detector, so that a smaller signal from a smaller sample volumes remains detectable. Thus, alterations suitable for use with smaller sample volumes include increasing the sensitivity of the light detector, or electronic detector; increasing the intensity of illumination used in analysis of smaller volumes of samples; increasing the path length through which light passes prior to detection by a detector; decreasing the distance between the sample and a detector; altering the wavelength of light, or detecting multiple wavelengths of light, passing thorough or absorbed by a smaller volume of sample; and other alterations.

Methods for reducing the volume of a sample used during sample analysis, e.g., reducing the amount of sample required for an assay for the detection of, or quantification of, a target substance in a sample, include methods in which a small sample is diluted with a diluent, such as water, or buffer, or other diluent. In this way, the volume of the material presented for analysis and detection may remain the same, or may be similar, to the volume that was initially used or required. Since a diluted sample may provide a smaller signal than an undiluted sample, similar modifications in light intensity, illumination wavelength, container configuration, container volume, sample placement, and other modifications may be used with a diluted sample.

Methods for reducing the volume of a sample used during sample analysis, e.g., reducing the amount of sample required for an assay for the detection of, or quantification of, a target substance in a sample, include methods in which a larger amount (absolute amount) of dye, or enzyme substrate, or other molecule used in producing a signal indicative of the presence, or amount, of a target molecule, is added to a small sample; or methods in which a larger concentration of dye, or enzyme substrate, or other molecule used in producing a signal indicative of the presence, or amount, of a target molecule, is added to a small sample; or a dye, enzyme substrate, or other molecule used in producing a signal indicative of the presence, or amount, of a target molecule, providing a more intense or stronger signal is added to a small sample, as compared to the original dye amount, concentration, or make-up.

Methods for reducing the volume of a sample, e.g., reducing the amount of sample required for an assay for the detection of, or quantification of, a target substance in a sample, include methods in which the optical properties of a sample container are altered so as to focus, or reflect, light impinging on the sample to provide increased light intensity to the sample (e.g., increased light intensity to a smaller volume, where the sample is a smaller volume sample) as compared to the optical properties and volumes of the original configuration. Thus, a sample container may be altered to include lenses, or lensing surfaces, which refract light onto a sample chamber, or onto a portion of a sample chamber, in which a sample is held. Thus, a sample container may be altered to include mirrors, or mirrored surfaces, which reflect light onto a sample chamber, or onto a portion of a sample chamber, in which a sample is held.

Accordingly, methods for reducing the amount of sample required for an assay for the detection of, or quantification of, a target substance in a sample, include the following methods.

Applicants disclose methods for reducing the volume of sample used in the performance of an assay for the detection of, or quantification of, a target substance in a sample, where the assay comprises optical detection of a target substance in a sample. Such methods may comprise, for example, reducing the volume of sample used in the assay from a first (larger) volume to a second (smaller) volume, where the assay was previously performed using a first volume of sample; and increasing the intensity of illumination applied to the sample. Such increased illumination is used to detect or quantify a target substance in the sample. Such a method may allow detection, quantification, or detection and quantification of the target substance in a reduced volume of sample, since many optical signals are enhanced at higher levels of illumination intensity. Such detection, quantification, or detection and quantification may include absorbance measurements, transmission measurements, turbidity measurements, polarization measurements, circular dichroism measurements, light scattering measurements, and other optical measurements. It will be understood that these, and other optical measurements, may be used for any of the methods, such as, e.g., any optical methods, disclosed herein.

Further methods for reducing the volume of sample used in the performance of an assay for the detection of, or quantification of, a target substance in a sample, include methods where the assay comprises detection of a fluorescent label. Such methods may comprise, for example, reducing the volume of sample used in the assay from a first volume to a second volume, wherein said second volume is less than said first volume, wherein the assay was previously performed using a first volume of sample; and increasing the intensity of light illuminating the sample and assay reagents during fluorescence measurements. Such methods may allow detection, quantification, or detection and quantification of the target substance in a reduced volume of sample, since fluorescence from many labels is enhanced at higher levels of illumination.

Thus, as disclosed herein, an increase in light intensity may be utilized in methods for reducing the volume of sample used in the performance of an assay for the detection of, or quantification of, a target substance in a sample. Light intensity may be increased from a light source by any suitable means. Providing an additional light source, or a plurality of additional light sources, is effective to increase the intensity of illumination applied to a sample. Increasing the power (e.g., by increasing the current, or by increasing the voltage, or both) applied to a light source is effective to increase the intensity of illumination applied to a sample. Providing a different light source, capable of providing increased light intensity, is effective to increase the intensity of illumination applied to a sample; for example, an original light source of a first type may be replaced by, e.g., an incandescent light source, a halogen light source, a laser light source, a diode light source, a sodium vapor light source, or other light source. Lenses, mirrors, prisms, fiber optics, and other optical elements may be provided effective to increase the intensity of illumination applied to a sample.

Further methods for reducing the volume of sample used in the performance of an assay for the detection of, or quantification of, a target substance in a sample, comprise assays comprising detection of a dye. Such methods, for example, may comprise reducing the volume of sample used in the assay from a first volume to a second volume, wherein said second volume is less than said first volume, wherein the assay was previously performed using a first volume of sample; and increasing the concentration of a dye added to the sample, where the dye labels a target substance in said sample. Such methods may allow detection, quantification, or detection and quantification of the target substance in a reduced volume of sample, since signals from many dyes or other labels are enhanced at higher concentrations.

In embodiments, methods for reducing the volume of sample used in the performance of an assay for the detection of, or quantification of, a target substance in a sample, may comprise detection of a dye. Such methods, for example, may comprise reducing the volume of sample used in the assay from a first volume to a second volume, wherein said second volume is less than said first volume, wherein the assay was previously performed using a first volume of sample; and increasing the amount of a dye added to the sample, where the dye labels a target substance in said sample. Such methods may allow detection, quantification, or detection and quantification of the target substance in a reduced volume of sample, since signals from many dyes or other labels are enhanced with greater amounts of dye.

Thus, as disclosed herein, dyes may be utilized in methods for reducing the volume of sample used in the performance of an assay for the detection of, or quantification of, a target substance in a sample. Dyes suitable for use in the methods disclosed herein include fluorescent dyes, chemiluminescent dyes, nuclear dyes, membrane dyes, Nile Blue, Coomassie blue, rhodamine dyes, fluorescein dyes, Sybr dyes, DRAQ5 and related dyes, fluorescent proteins (e.g., green fluorescent protein and related proteins), resazurin (7-Hydroxy-3H-phenoxazin-3-one 10-oxide); 10-acetyl-3, 7-dihydroxyphenoxazine (Amplex Red) and similar compounds (e.g., Amplex UltraRed (A36006 from Life Technologies, Carlsbad, Calif. 92008); resorufin compounds (e.g., 7-ethoxyresorufin); dyes such as e.g., fluorescein, calcein, rhodamine, and ethidium dyes; N-methyl-4-hydrazino-7-nitrobenzofurazan; acridinium (acridine-9-carboxylic acid) esters and compounds which react with these compounds to alter an optical property of a solution; phenols and phenol derivatives (e.g., p-iodophenol and p-phenylphenol); luminescent amines, including amine adducts (e.g., as may be derived from copper cyanide), silver stain, and other dyes and stains as disclosed herein and as known and used in the art.

Further methods for reducing the volume of sample used in the performance of an assay for the detection of, or quantification of, a target substance in a sample, may comprise detection of an enzymatic label. Such methods, for example, may comprise reducing the volume of sample used in the assay from a first volume to a second volume, wherein said second volume is less than said first volume, wherein the assay was previously performed using a first volume of sample; and increasing the concentration of substrate added in the presence of the enzyme prior to, or during enzymatic label measurements. Such methods may allow detection, quantification, or detection and quantification of the target substance in a reduced volume of sample, since signals from many enzymatic labels are enhanced at higher levels of substrate concentration.

Thus, as disclosed herein, enzymatic labels and substrates may be utilized in methods for reducing the volume of sample used in the performance of an assay for the detection of, or quantification of, a target substance in a sample. Enzymes and substrates suitable for use in the methods disclosed herein include horseradish peroxidase (the enzyme) and peroxide (the substrate). Although horseradish peroxidase is specifically recited herein, any peroxidase (and substrates of the peroxidase) that participates in a reaction with its substrate(s) to form a colored product may be used in the detection and/or quantification of an analyte in a sample. For example, the colorant horseradish peroxidase (HRP) participates in a reaction with any one or more of several molecules effective to change the optical properties of a solution to which the HRP is added (e.g., by changing the color, the absorbance of light through a solution to which the HRP is added, and/or other optical properties of the solution). For example, HRP may react with an aniline-containing compound such as N-Ethyl-N-(2-hydroxy-3-sulfopropyl)-3,5-dimethoxyaniline (ALPS), or with an aminoantipyrene compound such as 4-aminoantipyrene or with phenolic compounds. Thus, for example, a peroxidase (e.g., HRP, myeloperoxidase, or other peroxidase), an aniline-containing compound, and an aminoantipyrene may all be termed "colorants." In further examples, HRP may react with a benzidine-containing compound (e.g., with diaminobenzidine (DAB); tetramethylbenzidine (TMB); 2,2'-azino-bis(3-ethylbenzothiazoline-6-sulphonic acid) (DABS); 3-dimethylaminobenzoic acid (DMAB); hydroquinone; o-tolidine; o-phenylenediamine; o-chlorophenol; p-hydroxy-benzenesulfonate; p-anisidine; a Trinder reagent (such as 4-aminoantipyrene, methylbenzothiazolinonehydrazone (MBTH), or other compound for producing a Trinder dye); and derivatives and related compounds) to form a colored product. HRP or other peroxidase may also react with other compounds to form a chemiluminescent product; for example, HRP or other peroxidase may react with luminol to form a chemiluminescent product (other molecules may be present, and may enhance such reactions; for example, HRP-mediated production of luminescent products from luminol is enhanced in the presence of 4-iodophenol). It will be understood that other enzymes and reactants may be used to form colored products useful for the detection of an analyte in a sample.

Alkaline phosphatase reagents are commercially available; for example, Nitroblue Tetrazolium (NBT) is used with the alkaline phosphatase substrate 5-Bromo-4-Chloro-3-Indolyl Phosphate (BCIP) to provide a colored product which may be observed and quantitated. Other reagents include Fast Red TR/Naphthol AS-MX and TR phosphate (4-Chloro-2-methylbenzenediazonium/3-Hydroxy-2-naphthoic acid 2,4-dimethylanilide phosphate, reagents for the production of p-nitrophenol, and others known in the art may be used.

Further methods for reducing the volume of sample used in the performance of an assay for the detection of, or quantification of, a target substance in a sample, include methods where the assay comprises labeled antibody detection of a target substance. Such methods comprise, for example, reducing the volume of sample used in the assay from a first volume to a second volume, wherein said second volume is less than said first volume, wherein the assay was previously performed using a first volume of sample; and increasing the concentration of labeled antibody, or increasing the number of labels per antibody, or altering the label to provide a more detectable signal. Such methods may allow detection, quantification, or detection and quantification of the target substance in a reduced volume of sample, since signals from more, or more highly labeled, or more detectably labeled antibodies are enhanced as compared to signals provided by the original methods.

Methods for labeling antibodies are known in the art, including methods for providing multiple labels, or different labels, on antibodies. Methods of conjugating labels and other moieties to antibodies and other proteins are discussed, for example, in Wofsy et al. Selected Methods in Cellular Immunology, p. 287, Mishel and Schiigi (eds.) San Francisco: W. J. Freeman Co. (1980)); Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., Immunol. Rev., 62:119-58 (1982).

Further methods for reducing the volume of sample used in the performance of an assay for the detection of, or quantification of, a target substance in a sample, include assays comprising detection of an optical signal produced by a target substance, or by a reagent which binds to or reacts with the target substance. Such methods comprise, for example, reducing the volume of sample used in the assay from a first volume to a second volume, wherein said second volume is less than said first volume, wherein the assay was previously performed using a first volume of sample; and increasing the sensitivity of an optical detector used to detect a signal indicative of the presence or, or amount of, target substance in the sample. Such a method may allow detection, quantification, or detection and quantification of the target substance in a reduced volume of sample, since increased sensitivity to signals indicative of the presence or, or amount of, target substance in a sample will allow detection and quantification from smaller or less intense signals, such as those signals expected from smaller volume samples.

In embodiments, an optical detector may be located so as to be able to receive and to detect light coming from, or light passing through, a sample container. In embodiments, an optical detector is located outside a sample container. In embodiments, an optical detector may be operably connected with a fiber-optic conduit effective that light carried by the fiber optic conduit may be directed to the optical detector, and may be detected by the optical detector. In embodiments, the optical detector, or a fiber-optic conduit, may be located at least partially within a sample container, e.g., at least partially within an insert cavity of a sample container.

The sensitivity of a detector may be increased by providing additional sensors or detectors; by replacing a less-sensitive detector or sensor with a more-sensitive detector or sensor; by providing lenses, mirrors, or other optical enhancements which collect or focus a signal and direct it to the sensor or detector; by reducing "noise" in the sensor or detector (e.g., by cooling the sensor or detector, or by filtering the power driving the sensor or detector, or by other means); and by other means.

A related method for reducing the volume of sample used in the performance of an assay for the optical detection of, or optical quantification of, a target substance in a sample, comprises reducing the volume of sample, and decreasing the separation between the sample and an optical detector used to detect a signal indicative of the presence or, or amount of, target substance in the sample. Such a method may allow detection, quantification, or detection and quantification of the target substance in a reduced volume of sample, since such a reduced separation allows detection smaller signals indicative of the presence or, or amount of, target substance in a sample, such as those signals expected from smaller volume samples.

Further methods for reducing the volume of sample used in the performance of an assay for the detection of, or quantification of, a target substance in a sample, include methods where the assay comprises detection of optical absorbance produced by a target substance, or by a target substance and a reagent which binds to or reacts with the target substance. Such methods may comprise reducing the volume of sample used in the assay from a first volume to a second volume, wherein said second volume is less than said first volume, wherein the assay was previously performed using a first volume of sample; and increasing the path length within the sample between a source of illumination and through the sample to an optical detector used to detect an absorbance signal indicative of the presence or, or amount of, target substance in the sample. Increasing the optical path length through the sample provides a larger signal, since more sample is traversed by the light traveling along the longer path through the sample.

Such a method may allow detection, quantification, or detection and quantification of the target substance in a reduced volume of sample, since such an increased path length through the sample would allow detection smaller signals indicative of the presence or, or amount of, target substance in a sample, such as those signals expected from smaller volume samples. In embodiments, such an increased path length may be provided, even for a reduced volume sample, by, for example, providing a cuvette or other sample container having a long, narrow chamber, in which the sample resides and along the long portion of which the illumination is provided. Such a cuvette or sample container comprises an altered chamber dimension as compared to a cuvette or sample container as used in the assay for larger volume samples. In embodiments, such an increased path length may be provided, even for a reduced volume sample, by, for example, providing a mirror or mirrored surface at a position at or near a wall of the cuvette or other sample container, so that light from an illumination source follows a longer path, including a reflected portion, within the sample resides prior to detection of the light for an absorption measurement. Such a longer path for use with a reduced volume sample is longer as compared to a path for absorption measurements for larger volume samples.

Further methods for reducing the volume of sample used in the performance of an assay for the detection of, or quantification of, a target substance in a sample, include methods where the assay comprises detection of an optical signal produced by a target substance, or by a reagent which binds to or reacts with the target substance. Such methods may comprise reducing the volume of sample used in the assay from a first volume to a second volume, wherein said second volume is less than said first volume, wherein the assay was previously performed using a first volume of sample; and altering the wavelength of light, or detecting multiple wavelengths of light, passing through or absorbed by a smaller volume of sample. Such a method may allow detection, quantification, or detection and quantification of the target substance in a reduced volume of sample, since such an altered light wavelength, or such a plurality of wavelengths, allow detection smaller signals indicative of the presence or, or amount of, target substance in a sample, such as those signals expected from smaller volume samples.

Alteration of wavelengths of light may be accomplished by altering a light source; by passing light from a light source through a filter, or through a prism, or other optical element; by providing one or more additional light source(s); or any combination of these, among other methods which may be used to alter light wavelengths used to illuminate a sample.

Further methods for reducing the volume of sample used in the performance of an assay for the optical detection of, or optical quantification of, a target substance in a sample, include altering the polarization of light used to illuminate a sample. Such methods may comprise reducing the volume of sample used in the assay from a first volume to a second volume, wherein said second volume is less than said first volume, wherein the assay was previously performed using a first volume of sample; and altering the polarization of light passing through or absorbed by a smaller volume of sample. Such a method may allow detection, quantification, or detection and quantification of the target substance in a reduced volume of sample, since such altered light polarization allows detection signals indicative of the presence or, or amount of, target substance in a sample, such as those signals expected from smaller volume samples.

Altering the polarization of light may be accomplished, for example, by altering a light source; by passing light from a light source through a filter, or through a prism, or grating, or slit (or slits), or other optical element; by reflecting light from a surface; or any combination of these, among other methods which may be used to alter the polarization of light used to illuminate a sample.

Applicants further disclose a method for reducing the volume of sample used in the performance of an assay for the detection of, or quantification of, a target substance in a sample, where the assay comprises detection of an electrical signal produced by a target substance, or by a reagent which binds to or reacts with the target substance, the method comprising:

Reducing the volume of sample used in the assay from a first volume to a second volume, wherein said second volume is less than said first volume, wherein the assay was previously performed using a first volume of sample; and increasing the electronic amplification of an electrical detector used to detect an electrical signal indicative of the presence or, or amount of, target substance in the sample. Such a method may allow detection, quantification, or detection and quantification of the target substance in a reduced volume of sample, since such an increased electronic amplification of such an electrical detector would allow detection smaller signals indicative of the presence or, or amount of, target substance in a sample, such as those signals expected from smaller volume samples. Electrical detectors include, without limitation, ion-selective electrodes, amperometric detectors, and voltammetric detectors. Such detectors provide electronic output, and amplification of signals from such detectors may be performed by standard electronic techniques and devices. Amperometric techniques are discussed, for example, in "Amperometric Techniques" by Thomas Roussel et al., in the *Encyclopedia of Microfluidics and Nanofluidics*, pages 39-47, Springer Verlag (2008). Voltammetric techniques are discussed, for example, in Kounaves, "Voltammetric Techniques", Chapter 37 (pages 709-725) in: *Handbook of Instrumental Techniques for Analytical Chemistry*, edited by Frank Settle, Prentice-Hall (1997). Ion-selective electrodes are discussed, for example, in *Primer: Ion selective measurement in online analysis*, by YSI, a Xylem brand (2012) (available at: http://www.ysi.com/media/pdfs/ba76001-Online-ISE-Primer-e01.pdf).

In embodiments, an ion-selective electrode may be, e.g., a sodium-selective electrode, a potassium-selective electrode, a chloride-selective electrode, or other ion-selective electrode. An amperometric detector or a voltammetric detector may be used to detect the presence or concentration of ions or small molecules in a sample; for example, an amperometric or voltammetric detector may be used to detect the presence or concentration of, e.g., oxygen, an amino acid such as glutamate or dopamine, a drug such as aspirin or acetaminophen, a natural compound such as caffeine, or other element or molecule in a sample. In embodiments, an ion-selective electrode, an amperometric detector, or a voltammetric detector may be disposed at least partially within a sample container, e.g., within an insert cavity of a sample container. In embodiments, a portion, e.g., a tip, of an ion-selective electrode, an amperometric detector, or a voltammetric detector may be disposed at least partially within a sample container, e.g., within an insert cavity of a sample container.

A method for reducing the volume of sample used in the performance of an assay for the detection of, or quantification of, a target substance in a sample, the method comprising:

Reducing the volume of sample used in the assay from a first volume to a second volume, wherein said second volume is less than said first volume, wherein the assay was previously performed using a first volume of sample; and increasing the temperature of the assay. Such a method may allow detection, quantification, or detection and quantification of the target substance in the reduced volume of sample, since many labels and labeling reactions are enhanced at higher temperatures than at lower temperatures. For example, where photodetection of an enzymatic label (e.g., alkaline phosphatase, horse radish peroxidase, or other enzymatic label) in which the rate of production of a detectable product may be temperature sensitive, increased signal may be produced by reaction at higher temperatures. For example, where an assay is performed at room temperature (e.g., near 20° C.), increasing the assay temperature to about 25° C., or about 30° C., or about 32° C., or about 34° C., or about 35° C., or about 36° C., or about 37° C., or about 38° C., or about 39° C., or about 40° C., or higher, may increase the signal produced by an otherwise unchanged reaction.

Reducing the Time Required to Perform an Assay

Reducing the amount of time required to perform an assay (while maintaining the accuracy or precision of the assay) allows for processing more samples in a unit time than would otherwise be possible. Methods for reducing assay duration are discussed, for example, in U.S. Patent Applications 61/858,589, filed Jul. 25, 2013; U.S. Patent Application 61/903,346, filed Nov. 12, 2013; and U.S. patent application Ser. No. 14/341,422, filed Jul. 25, 2014, the contents of all of which applications are hereby incorporated by reference in their entireties.

Methods for reducing the amount of time required to perform an assay for the detection of, or quantification of, a target substance in a sample, include, but are not limited to, the following methods.

A method for reducing the time required for the performance of an assay for the detection of, or quantification of, a target substance in a sample, the method comprising:

Increasing the Temperature of the Assay

A further method for reducing the time required for the performance of an assay for the detection of, or quantification of, a target substance in a sample, the method comprising:

Reducing the volume of sample used in the assay from a first volume to a second volume, wherein said second volume is less than said first volume, and wherein the assay was previously performed using a first volume of sample; and increasing the temperature of the assay.

Such methods may allow detection, quantification, or detection and quantification of the target substance in the sample, since many the rate of reactions producing labels and labeling reactions are increased at higher temperatures than at lower temperatures. For example, where photodetection of an enzymatic label (e.g., alkaline phosphatase, horse radish peroxidase, or other enzymatic label) in which the rate of production of a detectable product may be temperature sensitive, a detectable amount of signal may be produced more quickly at higher temperatures than at lower temperatures. For example, where an assay is performed at room temperature (e.g., near 20° C.), increasing the assay temperature to about 25° C., or about 30° C., or about 32° C., or about 34° C., or about 35° C., or about 36° C., or about 37° C., or about 38° C., or about 39° C., or about 40° C., or higher, may reduce the amount of time required to produce a detectable amount of the signal, as compared to the original (lower temperature) reaction.

Devices for Reducing the Volume of a Sample (e.g., Inserts)

Sample analysis devices, and sample analysis systems including sample analysis devices, typically have one or more sample containers which are configured to hold a sample during sample analysis (e.g., during processing, or during analyzing, or both). Applicants disclose herein devices, systems, and methods for reducing the volume of sample required for, or used in, sample analysis.

Embodiments of these devices for reducing the amount of sample needed or used for sample analysis include inserts configured to fit inside a sample container, and to provide a chamber in which a sample—of smaller volume than the volume of sample held by the sample container—may be held during analysis by a sample analysis device or sample analysis system. The sample container with an insert within it, and sample within the insert, may be used to perform sample analysis of the sample in the insert. Thus, a sample container with an insert within it, and sample within the insert, may be used to perform processing steps, analyzing steps, or both processing steps and analyzing steps on the sample in the insert.

Embodiments of devices for reducing the amount of sample needed or used for sample analysis include inserts configured to replace a sample container, and to provide a smaller chamber than the one in the sample container. A sample—of smaller volume than the volume of sample held by the sample container—may be held in an insert that replaces a sample container during analysis by a sample analysis device or sample analysis system.

A sample container includes a cavity, or internal chamber, which may hold a sample. A sample container is typically designed so that fluid (e.g., a sample) held within the sample container is retained by gravity; that is, the wall or walls of the cavity are typically vertical, or nearly vertical, when the sample container is in use. A sample container has an opening through which a sample may be introduced into the bore of the sample container; the opening may define a plane, and the "width" the opening may be termed as being in an orientation that is substantially parallel to the plane of the opening. Thus, in order to introduce a sample into the cavity of a sample container, the sample passes through the plane of the opening (e.g., along a path substantially perpendicular to the plane of the opening). The "depth" of the cavity of a sample container may be termed as being in an orientation substantially perpendicular to the plane of the opening.

A device placed within the cavity, or internal chamber, of a sample container reduces the volume within the sample container that is available to hold the sample. Thus, placing an object or device within a sample container reduces the effective volume of the sample container cavity and reduces the volume of sample that may be held within the sample container. An object of any shape able to fit within the sample container, while leaving some volume available to hold a sample, may be used to reduce the volume of sample used in the performance of an assay. In embodiments, such an object may be an insert configured to fit within a sample container, where the insert includes a cavity or chamber configured to hold a sample. Placement of such an insert is effective to reduce the internal volume available to hold a sample.

Accordingly, Applicants disclose herein designs and descriptions for inserts to be placed within a cavity of a sample container, thereby to reduce the effective volume of the cavity of a sample container, and thus to reduce the volume of sample used or required for the performance of sample analysis. For example, an insert configured to fit within a sample container may fit snugly within the cavity, or chamber, of a sample container, leaving little or no space between the outer wall of the insert and the inner wall of the sample container's cavity or chamber. For example, such an insert may be configured to fit snugly within a sample container and have a cavity or chamber which is configured to hold a sample with little risk of loss due to leakage, or spillage. An insert fits within the cavity of a sample container. The wall or walls of such an insert define its cavity, termed an "insert cavity"; an insert cavity has a smaller volume than the cavity of the sample container. In embodiments, the walls of an insert, and an insert cavity within an insert, may be configured to allow transmission of light or other signals through the insert. In embodiments, an insert configured to allow transmission of light or other signals through the insert is configured to allow such transmission with little loss of light intensity, or with little distortion, or with little effect on light polarization, or combinations thereof.

A sample container (e.g., an original sample container as supplied with, or commonly used with, a sample analysis device) may have a cavity for holding a sample, and the volume of such a cavity may be, for example, about 500 µL, or about 1 mL, or about 2 mL, or about 3 mL, or about 5 mL, or about 10 mL, or more. An insert configured to fit within the cavity of an original sample container has an insert cavity; the volume of such an insert cavity will be less than the volume of the cavity of an original sample container. Placement of an insert in to the cavity of an original sample container is effective to reduce the volume of sample that is required, or that is used, during sample analysis. Such placement of an insert into the cavity of an original sample container provides a smaller volume cavity for holding sample during sample analysis; use of the smaller-volume "insert cavity" of the insert thus enables sample analysis requiring or using less sample than would be required, or used, with an original sample container.

Thus, the insert cavity (the internal cavity of an insert configured to fit within the cavity of a sample container) may have a volume of less than about 500 µL, or less than about 400 µL, or less than about 300 µL, or less than about 250 µL, or less than about 200 µL, or less than about 150 µL, or less than about 100 µL, or less than about 50 µL, or less than about 25 µL, or less than about 15 µL, or less than about 10 µL, or less than about 5 µL, or less than about 4 µL, or less than about 3 µL, or less than about 2 µL, or less than about 1 µL, or less. Use of such an insert allows the handling and analysis of smaller volumes of sample than does the use of an original sample container. It will be understood that an original sample container may be replaced by a replacement sample container, or other sample container, where the replacement or other sample container has a cavity with a smaller volume than the volume of the cavity of the original sample container. In the following, the cavity of a replacement sample container, or other sample container, will also be referred to as an "insert cavity"; such an insert cavity has a volume that is less than the volume of the original sample container which is replaced by the replacement sample container, or other sample container. For example, a replacement sample container, or other sample container, may have an insert cavity having a volume of less than about 500 µL, or less than about 400 µL, or less than about 300 µL, or less than about 250 µL, or less than about 200 µL, or less than about 150 µL, or less than about 100 µL, or less than about 50 µL, or less than about 25 µL, or less than about 15 µL, or less than about 10 µL, or less than about 5 µL, or less than about 4 µL, or less than about 3 µL, or less than about 2 µL, or less than about 1 µL, or less.

An insert (or replacement sample container, or other sample container) may be made from glass (e.g., borosilicate glass, aluminosilicate glass, quarts, or other glass), or a plastic or acrylic compound (e.g., polymethyl methacrylate, or other acrylics), or a polymer (such as, e.g., polypropylene, polystyrene, polycarbonate, polyurethane, and other polymers), or combinations of these, or other material or combinations of materials. Preferred materials, such as acrylic compounds, provide good fluid flow, enhancing recovery of fluid from the well of the insert. In embodiments, such a material is translucent. In embodiments, such a material is transparent. In alternative embodiments, such a material may be opaque.

An example of an insert configured to fit within a sample container is shown in FIG. 1. Insert 110 has an insert cavity 120 defined by a vertical wall 130 and a floor 140. The opening 150 of the insert cavity 120 allows sample to be placed in, or removed from, the insert 110. The insert 110 has an outer wall 160 and a base 170, both of which are configured to fit within a sample container. The shape and orientation of the floor 140 may be flat, or may be beveled, or may be rounded, or may be a combination of such shapes, or may be a complex or an irregular shape. The outer wall 160 of an insert 110 is configured to fit within the cavity of a sample container; such an outer wall 160 may be vertical (e.g., as shown in the example shown in FIG. 1), or may be at an angle; for example, an outer wall may be angled so that the outer diameter of an insert is greatest near the opening, and smallest near the floor, or near the base of the insert. In embodiments, an insert may have a substantially cylindrical shape (e.g., as indicated in FIG. 1); or may have a tapered, or partially conical shape (e.g., where the diameter near the base is less than the diameter near the opening); or may have a square, or rectangular, or triangular, or other shape.

Reducing or eliminating the volume that is substantially inaccessible to a tube, needle, pipette tip, probe or sensor is an important consideration in the design of an insert. For example, a sample container will typically retain some amount of sample within the container after draining; the amount of sample left in the sample container (the dead volume) is typically lost for further use in sample analysis. Some sample containers may have dead volumes of about 200 µL, or about 100 µL, or about 50 µL; however, it is desirable to reduce the dead volume of a sample container.

In addition, some sample containers require there to be an amount of sample at the bottom of the container in order to fill the sample container up to a level accessible for measurements. Such sample containers thus require at least a minimum of sample volume within the container before a measurement of the sample may be made. Some sample containers may require about 200 µL, or about 100 µL, or about 50 µL, of sample in order for the sample level within the sample container to be high enough for measurement. The volume of the sample required to fill the sample container to the lowest level necessary in order for a measurement to be made is typically closely similar in magnitude to the dead volume of the sample container.

It is desirable to eliminate or reduce such sample volume that remains after draining a container, or that is used or required—but not measured—before a measurement may be obtained; thus, it is desirable to have a small a dead volume. It is desirable to reduce the amount of dead volume in a container to less than about 200 µL, or less than about 100 µL, or less than about 50 µL, or less than about 40 µL, or less than about 30 µL, or less than about 20 µL, or less than about 15 µL, or less than about 10 µL, or less than about 5 µL, or less than about 4 µL, or less than about 3 µL. In embodiments, it is desirable to have a sample container with a dead volume of less than about 50 µL, or less than about 40 µL, or less than about 30 µL, or less than about 20 µL, or less than about 15 µL, or less than about 10 µL, or less than about 5 µL, or less than about 4 µL, or less than about 3 µL.

Thus, it is desirable to reduce the volume of sample remaining in a sample container (after draining the container) to a small volume of sample. In embodiments, such a small volume of sample may comprise less than about 50 µL, less than about 40 µL, less than about 30 µL, or less than about 25 µL, less than about 20 µL, or less than about 15 µL, or less than about 10 µL, or less than about 5 µL, or less than about 4 µL, or less than about 3 µL, or less than about 2 µL, or less than about 1 µL, or less. This may be done by altering the size or the shape, or both, of the bore in which the sample is held. A bore may be altered so as to reduce the dead volume by providing a rounded (e.g., circular, or elliptical) horizontal cross-sectional shape; a bore may have a square or rectangular horizontal cross-sectional shape; or other horizontal cross-sectional shape.

A bore may have a volume; reducing the volume of the bore may reduce the dead volume of a bore, and may reduce the volume of sample remaining in a sample container (after draining the container) to a small volume of sample. The dead volume of a bore, and the volume of sample remaining in a sample container after draining, may be reduced by placement of an insert into the cavity of an original sample container, where the insert cavity has a smaller dead volume than the original sample container. The dead volume of a bore, and the volume of sample remaining in a sample container after draining, may be reduced by providing a replacement sample container having a smaller dead volume than the original sample container. Methods of analysis using containers having reduced dead volume, and having reduced volume of sample remaining in a sample container after draining, include methods of sample analysis, wherein an insert (placed in an original sample container), or replacement sample container, or other container, is used to hold a sample, and the sample is analyzed, where the insert, replacement sample container, or other container, has a smaller dead volume than does the original sample container, or has a reduced volume of sample remaining in a sample container after draining.

A sample container having a dead volume, or a volume of sample remaining in a sample container after draining, of less than about 200 µL, or less than about 100 µL, or less than about 50 µL, or less than about 40 µL, or less than about 30 µL, or less than about 20 µL, or less than about 15 µL, or less than about 10 µL, or less than about 5 µL, or less than about 4 µL, or less than about 3 µL or less than about 2 µL, or less than about 1 µL, or less, may be provided by placing an insert into a sample container having a larger dead volume, or in which a larger volume of sample remains after draining, where the insert has an insert cavity having a dead volume, or volume of sample remaining after draining, of less than about 200 µL, or less than about 100 µL, or less than about 50 µL, or less than about 40 µL, or less than about 30 µL, or less than about 20 µL, or less than about 15 µL, or less than about 10 µL, or less than about 5 µL, or less than about 4 µL, or less than about 3 µL or less than about 2 µL, or less than about 1 µL, or less.

A sample container having a dead volume, or volume of sample remaining after draining, of less than about 200 µL, or less than about 100 µL, or less than about 50 µL, or less than about 40 µL, or less than about 30 µL, or less than about 20 µL, or less than about 15 µL, or less than about 10 µL, or less than about 5 µL, or less than about 4 µL, or less than about 3 µL, or less than about 2 µL, or less than about 1 µL, or less, may be provided by replacing an original sample container (e.g., a previously-supplied sample container) with a replacement sample container, e.g., a sample container having a dead volume, or volume of sample remaining after draining, of less than about 200 µL, or less than about 100 µL, or less than about 50 µL, or less than about 40 µL, or less than about 30 µL, or less than about 20 µL, or less than about 15 µL, or less than about 10 µL, or less than about 5 µL, or less than about 4 µL, or less than about 3 µL or less than about 2 µL, or less than about 1 µL, or less.

Where a probe is to be placed within a bore of an insert or of a replacement sample container, or of any other sample container (e.g., during performance of an analysis of a sample), reducing the diameter or width of the bore to as closely approximate the diameter or width of the probe is useful to reduce the amount of inaccessible volume in the insert. Similarly, where a probe is to be placed within a bore of an insert or of a replacement sample container, or of any other sample container, reducing the depth of the bore to as closely approximate the depth achieved by the probe within the bore is useful to reduce the amount of inaccessible volume in the insert, replacement sample container, or other sample container.

Thus, the depth of an insert cavity of an insert, or of a replacement sample container, or of any other sample container is an important characteristic. The depth of an insert cavity, along with the width of an insert cavity, may be designed so as to reduce the total volume of the insert cavity, and also may be designed so as to reduce the volume of sample which may be inaccessible to a probe inserted into the insert cavity. Reducing the total volume of an insert cavity is a design goal for providing an insert, or replacement sample container, or other sample container suitable for reducing the amount of sample required for sample analysis. A further design goal for providing an insert or replacement sample container, or any other sample container suitable for reducing the amount of sample required for sample analysis is to reduce, or eliminate, the volume in the insert cavity that may be inaccessible to a probe placed in a sample in an insert cavity.

Accordingly, the shape of the floor of the insert cavity is a further consideration in the design of an insert or replacement sample container, or any other sample container. Providing a bevel at the base of the bore of an insert or replacement sample container, or any other sample container, may aid in allowing a probe to reach its maximum depth within a bore, while reducing the amount of inaccessible volume within the bore. In addition, a bevel may aid in fluid flow (e.g., flow into, or out of the insert cavity, or both). In embodiments, such a bevel may include a conic (e.g., triangular cross-section) bevel; a circular or hemispherical (e.g., a rounded or partly circular cross-section) bevel; an oval or elliptical (e.g., a rounded but not circular cross-section); or other shape. In embodiments, a bevel may include a combination of two or more such shapes (e.g., may include conic portions and may include circular portions; or may include flat portions and circular portions; or may include flat portions and conic portions).

Figure 2A:
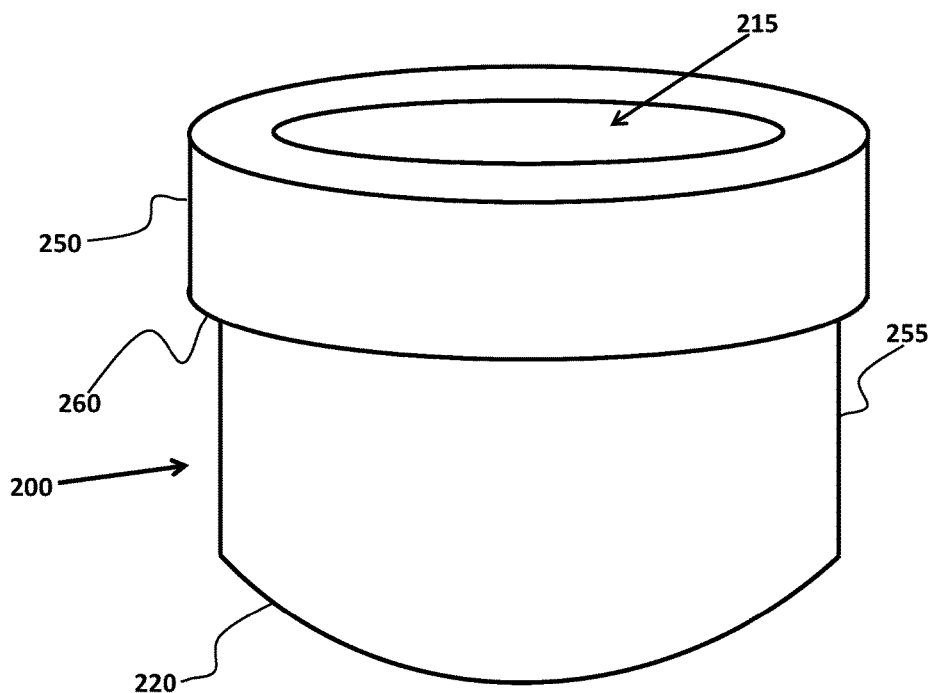
FIG. 2A shows a perspective view of an insert having features as disclosed herein.

An illustration of an exemplary insert having an insert cavity is shown in FIG. 2A. The perspective view of the insert 200 shows an opening 215 through which a sample may pass into the insert cavity 210 (shown in FIG. 2B). The insert 200 shown in FIG. 2A has an upper portion with an outer wall 250, a lower portion with an outer wall 255, and a lip 260. The exemplary insert 200 shown in FIG. 2A has a base 220 at its bottom. A lip 260 may be configured to lodge on a surface of a sample container when an insert 200 is placed within the sample container; thus, a lip 260 may help with the proper placement of an insert in a sample container, and so insure the proper operation of a sample analysis device or system in which an insert 200 is in place in a sample container. In embodiments, an insert 200 may have no lip 260, and the upper portion wall 250 may be flush with the lower portion wall 255. The walls 255 and 260 are shown as being vertical, i.e., perpendicular to the plane suggested by the opening 215. In embodiments, a lower portion wall 255 may be tapered, so that the insert 200 may be wider nearer the opening 215 than it is nearer the base 220. A wall 250 or 255, or both, may have other shapes and orientations as well; for example, an upper portion wall 250 may have a substantially vertical orientation (e.g., similar to that shown in FIG. 2A) while a lower portion wall 255 may be angled so as to taper from a wider to narrower along the wall in the upper to lower direction. In embodiments, an upper portion wall 250 may be tapered, while a lower portion wall 255 may have a substantially vertical orientation (e.g., similar to that shown in FIG. 2A). In embodiments, both an upper portion wall 250 and a lower portion wall 255 may be angled so as to taper; the upper taper may be the same as the lower taper, or the upper taper may be different than the lower taper. In embodiments, such tapers may become narrower towards the lower portion; in embodiments, such tapers may become wider towards the upper portion.

It will be understood that the designs and features of an insert cavity as shown in FIG. 2A apply equally to insert cavities of an insert, to a replacement sample container, and to any other sample container. Thus, the disclosure and discussion regarding FIG. 2A, and the disclosure and discussion regarding the other figures herein, may be applied to replacement sample containers, and to any other sample container, and cavities therein, as well as to inserts and their insert cavities.

Figure 2B:
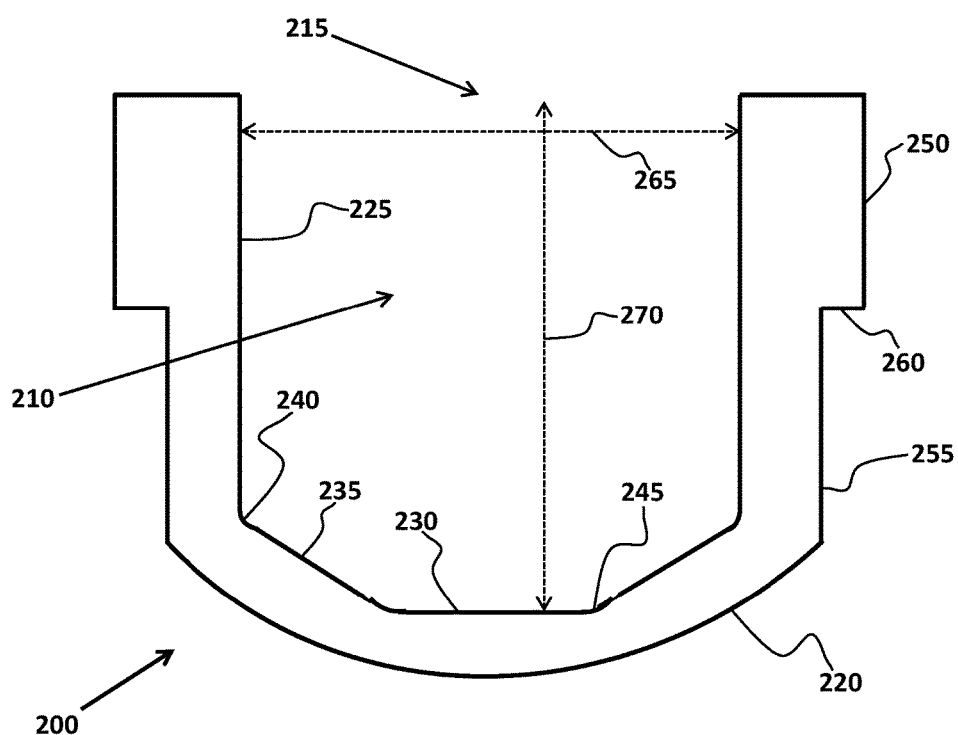
FIG. 2B shows a cross-section of an insert as shown in FIG. 2A, showing the insert cavity and illustrating an example of a bevel in the floor of an insert suitable for enhancing fluid flow and for reducing the volume of an insert cavity.

An illustration of an exemplary bevel in the bottom portion of an insert cavity is shown in FIG. 2B, which provides a cross-section of an insert 200 having features as disclosed herein. In the example shown, the floor 230 of the cavity 210 is flat, and has a flat bevel wall 235 disposed at an angle to the vertical inner wall 225 of the cavity 210. As shown, the junctions between the flat portions are rounded. In embodiments, the junctions between flat portions may not be rounded. As shown, the bottom portion of the insert cavity 210 includes a flat portion (floor 230) and rounded portions (wall angle 240 and floor angle 245). Wall angle 240 is the angle between inner wall 225 and bevel wall 235; floor angle 245 is the angle between bevel wall 235 and floor 230. In the example shown, floor 230 is perpendicular to inner wall 225, so that wall angle 240 and floor angle 245 are complementary. Thus, in the example shown in FIG. 2B, floor angle 245 is about 30° and wall angle 240 is about 60°. In embodiments of inserts having features as disclosed herein, floor angle 245 may be between about 10° to about 50° and wall angle 240 may be between about 80° to about 40°. In further embodiments of inserts having features as disclosed herein, floor angle 245 may be between about 25° to about 45° and wall angle 240 may be between about 65° to about 45°. In further embodiments, an inner wall 225 is not perpendicular to floor 230; in these embodiments, wall angle 240 and floor angle 245 will not be complementary. In embodiments, wall 225 need not be vertical; for example, it may be angled so that the width 265 of the cavity 210 is greater near the opening 215 than it is near to the floor 230. In the example shown in FIG. 2B, the depth 270 of cavity 210 is about the same as the width 265. In embodiments, the ratio of depth 270 to width 265 may be between about 0.1:1 to about 10:1 (i.e., from a ratio in which depth 270 is about one tenth the width 265, to a ratio in which depth 270 is about ten times the width 265). In embodiments, the ratio of depth 270 to width 265 may be between about 0.2:1 to about 5:1 (i.e., from a ratio in which depth 270 is about one fifth the width 265, to a ratio in which depth 270 is about five times the width 265). In embodiments, the ratio of depth 270 to width 265 may be between about 0.5:1 to about 3:1 (i.e., from a ratio in which depth 270 is about half the width 265, to a ratio in which depth 270 is about 3 times the width 265). In embodiments, the ratio of depth 270 to width 265 may be about 0.3:1; or about 0.5:1; or about 0.8:1; or about 1:1 (e.g., similar to that shown in FIG. 2B); or about 1.2:1; or about 1.5:1; or about 1.8:1; or about 2:1; or about 3:1; or about 4:1; or about 5:1; or about 6:1; or about 8:1; or other ratio.

It will be understood that the designs and features of an insert cavity as shown in FIG. 2B apply equally to insert cavities of an insert, to a replacement sample container, and to any other sample container. Thus, the disclosure and discussion regarding FIG. 2B, and the disclosure and discussion regarding the other figures herein, may be applied to replacement sample containers, and to any other sample container, and cavities therein, as well as to inserts and their insert cavities.

In further embodiments, an insert may be configured to completely replace an original sample container (e.g., such a replacement insert may be considered a replacement sample container). In such embodiments of devices for reducing the amount of sample needed or used for sample analysis, an insert may be configured to replace a sample container by having the same, or compatible outside dimensions as the sample container, and having an insert cavity as disclosed herein. The insert cavity of an insert configured to replace a sample container may be the same as an insert configured to fit within a sample container (e.g., the insert cavity of a replacement sample container may be sized and configured in the same was as described and disclosed herein regarding the insert cavities of sample container inserts). Thus, in embodiments, an insert configured to replace a sample container may have an insert cavity having the same dimensions, including the same ratio of depth to width, and the same taper, and the same bevel, as disclosed herein with respect to inserts configured to be placed within a sample container. An insert configured to replace a sample container (e.g., a replacement sample container) may be made from the same materials as disclosed herein as being suitable for inserts configured to be placed within a sample container.

Accordingly, inserts configured to be placed within a cavity of a sample container, or replacement inserts configured to substitute for a sample container, are effective to provide a smaller volume chamber for holding sample during sample analysis. Such inserts are effective to reduce the volume of sample required for the performance of sample analysis.

Methods of sample analysis include analyzing a sample using an insert, or replacement sample container, or any other sample container, to contain the sample during the sample analysis. Such methods include processing or analyzing a sample, or both, using an insert, or replacement sample container, or any other sample container, wherein the insert, or replacement sample container, or other sample container has an internal cavity with a small volume, so that only a small volume of sample is required for sample analysis. Such methods include processing or analyzing a sample, or both, using an insert, or replacement sample container, or any other sample container, wherein the insert, or replacement sample container, or other sample container has an internal cavity with a small dead volume, so that a large fraction of the sample within the internal cavity is available for sample analysis, and only a small amount, or a small fraction, of the sample within the internal cavity is unavailable for sample analysis.

For example, Applicants disclose herein a method of sample analysis with a sample analysis device using a sample container, wherein said sample is contained within said sample container during at least a portion of the performance of said sample analysis, said sample container comprising an internal cavity for holding said sample, said internal cavity having a volume, said internal cavity volume being less than about volume of less than about 500 μL, or less than about 400 μL, or less than about 300 μL, or less than about 250 μL, or less than about 200 μL, or less than about 150 μL, or less than about 100 μL, or less than about 50 μL, or less than about 25 μL, or less than about 15 μL, or less than about 10 μL, or less than about 5 μL, or less than about 4 μL, or less than about 3 μL, or less than about 2 μL, or less than about 1 μL, or less, the method comprising:
    placing a sample within said internal cavity of said sample container, and
    performing the sample analysis.

It will be understood that the sample analyzed as recited above may comprise the entire sample obtained from a subject, or may comprise a portion of the entire sample obtained from a subject. It will be understood that the sample analysis may include processing, analyzing, or both.

In embodiments, the internal cavity of the sample container recited in the above method as disclosed herein comprises the internal cavity of an insert; the insert may be disposed within the cavity of an original sample container. In embodiments, the internal cavity of the sample container recited in the above method as disclosed herein comprises the internal cavity of a replacement sample container. In embodiments, the internal cavity of the sample container recited in the above method as disclosed herein comprises the internal cavity of another sample container.

Applicants further disclose a method of sample analysis with a sample analysis device using a sample container, wherein said sample is contained within said sample container during at least a portion of the performance of said sample analysis, said sample container comprising an internal cavity for holding said sample, said internal cavity having a dead volume, said dead volume being less than about 200 μL, less than about 100 μL, or less than about 50 μL, or less than about 30 μL, or less than about 20 μL, or less than about 15 μL, or less than about 10 μL, or less than about 5 μL, or less than about 4 μL, or less than about 3 μL, or less than about 2 μL, or less than about 1 μL, or less, the method comprising:
    placing a sample within said internal cavity of said sample container, and
    performing the sample analysis.

It will be understood that the sample analyzed as recited above may comprise the entire sample obtained from a subject, or may comprise a portion of the entire sample obtained from a subject. It will be understood that the sample analysis may include processing, analyzing, or both.

In embodiments, the internal cavity of the sample container recited in the above method as disclosed herein comprises the internal cavity of an insert; the insert may be disposed within the cavity of an original sample container. In embodiments, the internal cavity of the sample container recited in the above method as disclosed herein comprises the internal cavity of a replacement sample container. In embodiments, the internal cavity of the sample container recited in the above method as disclosed herein comprises the internal cavity of another sample container.

A method of sample analysis with a sample analysis device having a sample container, wherein said sample is contained within said sample container during at least a portion of the performance of said sample analysis, said sample container comprising an internal cavity for holding said sample said internal cavity comprising a bevel in the bottom portion of an insert cavity, wherein the cross-sectional shape of said bevel comprises a triangular, circular, hemispherical, oval, elliptical, or other shape, the method comprising:
    placing a sample within said internal cavity of said sample container, and
    performing the sample analysis.

It will be understood that the sample analyzed as recited above may comprise the entire sample obtained from a subject, or may comprise a portion of the entire sample obtained from a subject. It will be understood that the sample analysis may include processing, analyzing, or both.

In embodiments, the internal cavity of the sample container recited in the above method as disclosed herein comprises the internal cavity of an insert; the insert may be disposed within the cavity of an original sample container. In embodiments, the internal cavity of the sample container recited in the above method as disclosed herein comprises the internal cavity of a replacement sample container. In embodiments, the internal cavity of the sample container recited in the above method as disclosed herein comprises the internal cavity of another sample container.

A method of sample analysis with a sample analysis device having a sample container, wherein said sample is contained within said sample container during at least a portion of the performance of said sample analysis, said sample container comprising an internal cavity for holding said sample, said internal cavity comprising an angle effective to provide a taper in at least an upper portion, or a lower portion, or both, of a wall of said internal cavity, wherein the taper comprises tapers selected from tapers in which the upper taper the same as the lower taper; the upper taper is different than the lower taper; tapers which become narrower towards the lower portion; and tapers which become wider towards the lower portion; the method comprising:

placing a sample within said internal cavity of said sample container, and performing the sample analysis.

It will be understood that the sample analyzed as recited above may comprise the entire sample obtained from a subject, or may comprise a portion of the entire sample obtained from a subject. It will be understood that the sample analysis may include processing, analyzing, or both.

In embodiments, the internal cavity of the sample container recited in the above method as disclosed herein comprises the internal cavity of an insert; the insert may be disposed within the cavity of an original sample container. In embodiments, the internal cavity of the sample container recited in the above method as disclosed herein comprises the internal cavity of a replacement sample container. In embodiments, the internal cavity of the sample container recited in the above method as disclosed herein comprises the internal cavity of another sample container.

A method of sample analysis with a sample analysis device having a sample container, wherein said sample is contained within said sample container during at least a portion of the performance of said sample analysis, said sample container comprising an internal cavity for holding said sample, said internal cavity comprising a bevel, a wall, a floor, and a wall angle formed by said wall and said bevel, wherein the wall angle comprises an angle of between about 80° to about 40°, or between about 65° to about 45°, the method comprising:

placing a sample within said internal cavity of said sample container, and performing the sample analysis.

It will be understood that the sample analyzed as recited above may comprise the entire sample obtained from a subject, or may comprise a portion of the entire sample obtained from a subject. It will be understood that the sample analysis may include processing, analyzing, or both.

In embodiments, the internal cavity comprises a floor angle formed by the floor and the bevel; and in embodiments, the wall angle is complementary to the floor angle.

In embodiments, the internal cavity of the sample container recited in the above method as disclosed herein comprises the internal cavity of an insert; the insert may be disposed within the cavity of an original sample container. In embodiments, the internal cavity of the sample container recited in the above method as disclosed herein comprises the internal cavity of a replacement sample container. In embodiments, the internal cavity of the sample container recited in the above method as disclosed herein comprises the internal cavity of an other sample container.

A method of sample analysis with a sample analysis device having a sample container, wherein said sample is contained within said sample container during at least a portion of the performance of said sample analysis, said sample container comprising an internal cavity for holding said sample, said internal cavity comprising a depth and a width, wherein the ratio of the depth to the width is between about 0.1:1 to about 10:1; between about 0.2:1 to about 5:1; or between about 0.5:1 to about 3:1; or may be about 0.3:1; or may be about 0.5:1; or may be about 0.8:1; or may be about 1:1; or may be about 1.2:1; or may be about 1.5:1; or may be about 1.8:1; or may be about 2:1; or may be about 3:1; or may be about 4:1; or may be about 5:1; or may be about 6:1; or may be about 8:1; or may be another ratio, the method comprising:

placing a sample within said internal cavity of said sample container, and performing the analysis.

It will be understood that the sample analyzed as recited above may comprise the entire sample obtained from a subject, or may comprise a portion of the entire sample obtained from a subject. It will be understood that the sample analysis may include processing, analyzing, or both.

In embodiments, the internal cavity of the sample container recited in the above method as disclosed herein comprises the internal cavity of an insert; the insert may be disposed within the cavity of an original sample container. In embodiments, the internal cavity of the sample container recited in the above method as disclosed herein comprises the internal cavity of a replacement sample container. In embodiments, the internal cavity of the sample container recited in the above method as disclosed herein comprises the internal cavity of another sample container.

Kits for Reducing the Volume of a Sample

A device, or devices, which may be inserted into a sample container may be provided as part of a kit; thus a kit may include an insert as disclosed herein, or may include a plurality of such inserts. In embodiments, a kit may include a replacement sample container as disclosed herein, or may include a plurality of such replacement sample containers. In embodiments, a kit may include another sample container, or may include a plurality of other sample containers. In embodiments, a plurality of the replacement sample containers are coupled together in a predetermined configuration such as but not limited to a ring of such containers, a disc with a plurality of such containers, partial ring of such containers, or other geometric configuration defined by coupling containers together. In one non-limiting example, the coupling together of containers may be by way of connecting elements, by forming the containers formed together with connecting elements, or using other manufacturing techniques to connect the containers together. This grouping of containers may facilitate the process of installing a plurality of such sample containers. Optionally, the common grouping may also be used to facilitate installation of a plurality of inserts.

In embodiments, a kit may include instructions for the use of the inserts, replacement sample containers, and other sample containers, including instructions for placement of the inserts into a sample container, instructions for cleaning an insert, and other instructions. A kit may include materials for maintaining, including materials for cleaning, an insert. A kit may include tools useful for placing an insert into a sample container, or for removing an insert from a sample container. A kit may include materials useful for securing, or for the secure placement of an insert into a sample container, or for insuring that an insert remains in place within a sample container after placement. A kit may include reagents for use with the inserts and with a sample container.

For example, instructions for the use of the inserts may include such information as that it may be desirable to insure that an insert is fully in place within a sample container before use; or that it may be desirable to clean (e.g., rinse with detergent, or solvent, followed by a rinse with water, such as de-ionized water; or to a rinse with water without use of detergents or solvents) prior to placement within a sample container; and other instructions. A kit may include instructions for the proper handling of an insert (e.g., use of gloves to avoid contamination during placement) of an insert into a sample container.

A kit may include materials for maintaining, including materials for cleaning, an insert. For example, where the insert may be cleaned with a detergent or solvent, the detergent or solvent may be provided as part of a kit. Water, such as de-ionized water, may be provided as part of a kit. A kit may include tools useful for handling an insert; for example, tongs or clamps (which may include, e.g., elongated handles for ease of placement of an insert in a location that is otherwise difficult to access by hand). A kit may include clamps, or tape, or shims, or other materials which may be useful for securing an insert in a sample container. A kit may include reagents (e.g., diluents, reactants, or other reagents) for use with the inserts and with a sample container.

Systems for Reducing the Volume of a Sample

Figure 3A:
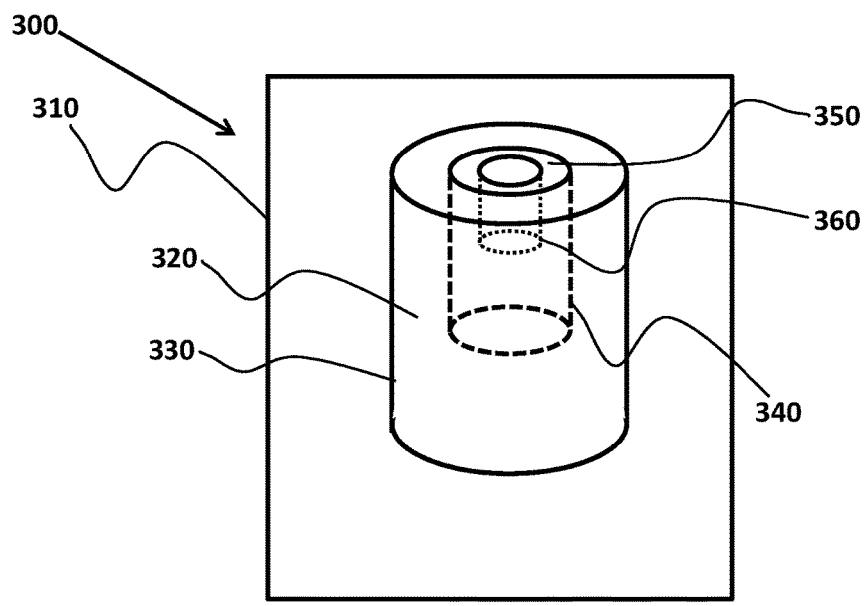
FIG. 3A provides an illustration of a system including an analysis device, a sample container, and an insert configured to fit within the sample container. The sample is held in the insert cavity of the insert, and so a smaller amount of sample is used than would be used in the absence of the insert. Such a system is able to analyze a smaller sample than would otherwise be required in the absence of the insert placed in the sample container.

Systems for reducing the volume of sample required for sample analysis include an analysis device, a sample container, and an insert for placement within a sample container. In embodiments, systems for reducing the volume of sample required for sample analysis include an analysis device, a sample container, and a replacement sample container. In embodiments, systems for reducing the volume of sample required for sample analysis include an analysis device, a sample container, and another sample container. As discussed above, a device as disclosed herein may be provided for placement within the cavity, or chamber, of a sample container, effective to reduce the volume within the sample container. The sample container, with insert, may be placed within an analysis device, and a sample placed in the sample container (i.e., within the insert disposed within the sample container) and the sample analyzed. In this way, a system is provided effective to analyze a sample, where the volume of the sample required or analysis is reduced as compared to the volume required by the analysis device in the absence of the insert, and in the absence of the use of methods disclosed herein. Such an insert, as disclosed herein, reduces the volume of the sample container and reduces the volume of sample that may be held within the sample container. Thus, systems comprising an insert (including any insert of any shape suitable to fit within a sample container, while leaving some volume available to hold a sample), may be used to reduce the volume of sample used in the performance of sample analysis. Thus, systems comprising a replacement sample container may be used to reduce the volume of sample used in, or required for, the performance of sample analysis. Thus, systems comprising another sample container may be used to reduce the volume of sample used in, or required for, the performance of sample analysis. FIG. 3A provides an illustration of a system including an analysis device, a sample container, and an insert configured to fit within the sample container. An analysis system 300 is shown, including an analysis device 310, which uses a sample container 320 having outer wall 330 to hold a sample during analysis. Sample container 320 has a cavity 340 defined by an inner wall of the sample container (shown with dashed lines). Fitted within the sample container cavity 340 is an insert 350; the insert 350 has an insert cavity 360 (shown with dotted lines).

The sample container 320 (with the insert 350 in place within the cavity 340 of the sample container) is in place within the analysis device 310, effective that a sample may be analyzed by the analysis device 310. However, with the insert 350 in place within the cavity 340 of the sample container 320, the volume of sample that is analyzed is less than the volume of sample that would have been required if the insert 350 had not been placed within the cavity 340 of the sample container 320.

An insert is thus configured to reduce the sample volume required for sample analysis by an analysis device or an analysis system. In embodiments, an insert has features as disclosed herein, and is configured to enhance fluid flow in the insert cavity. In embodiments, an insert has features as disclosed herein, and is configured both to reduce the sample volume required for sample analysis by an analysis device or analysis system, and to enhance fluid flow in the insert cavity.

Figure 3B:
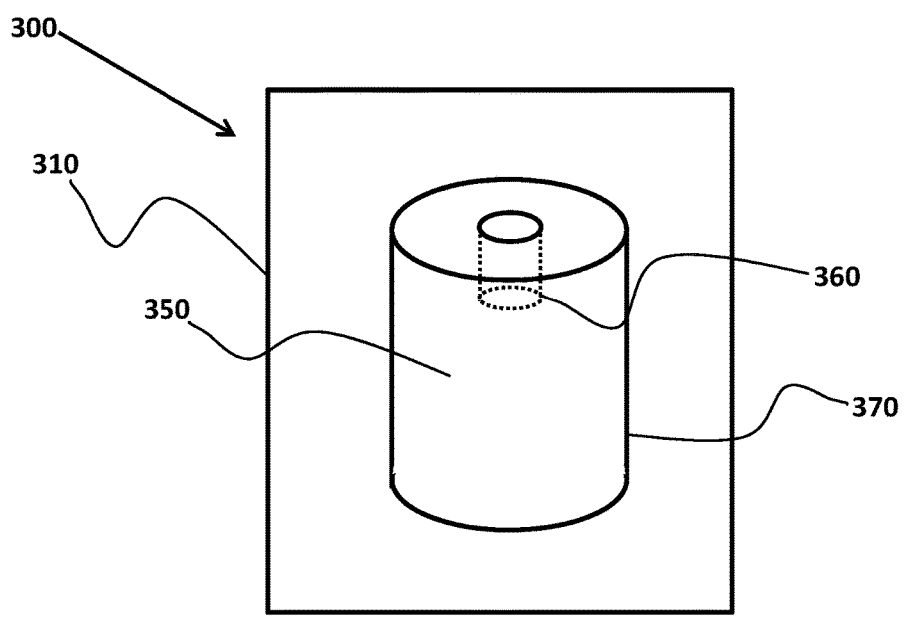
FIG. 3B provides an illustration of a system including an analysis device, a sample container, and an insert configured to fit within the analysis device, in place of a sample container. Such a system is able to analyze a smaller sample than it would otherwise be able to do in the absence of the insert, which is used to hold the sample during analysis instead of the sample container.

FIG. 3B provides an illustration of an analysis system 300 including an analysis device 310, but without a sample container. In place of a sample container, a sample is held by an insert 350 configured to replace the sample container; analysis by sample analysis device 310 proceeds with the sample held in insert cavity 360 (shown with dotted lines) within the insert 350. The outer wall 370 of the insert 350 that replaces a sample container has dimensions and shape that is compatible with the analysis device 310; thus, outer wall 370 of the insert 350 is, as far as is necessary to operably fit in analysis device 310, the same as outer wall 330 of the sample container as shown in FIG. 3A.

Insert 350, positioned in place of a sample container within the analysis device 310, is effective to hold a small volume of sample for analysis by analysis device 310. The volume of sample that is analyzed in this way is less than the volume of sample that would have been required if the insert 350 had not been used in place of the sample container (e.g., sample container 320).

Applicants have performed experiments using commercial analysis devices by modifying some aspects of the hardware and some aspects of the software in order to customize assays used to analyze blood samples. General approaches used in these modifications include, for example, reducing the final volume read by the detector; optimization of the dilution levels for each assay; not using the ion selective electrode detectors; optimizing the chloride content of reagents and optimizing the protocols which use chloride-containing reagents; modifying the design of the sample container to reduce sample volume and to reduce overage (e.g., reduce the risk of spills or wasted sample); including a predilution step in order to predilute the plasma in the sample containers; selecting which assays should be done in solutions containing a first anticoagulant such as but not limited to EDTA and which in solutions of a second and different anticoagulant such as but not limited to heparin, in order to meet the assay requirements while at the same time also minimizing sample volume desired for each assay. Such modifications were aimed at optimizing assay protocols so as to minimize overages in dilution vessels and in pipetting operations.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013-2014 Theranos, Inc.

We claim:

1. A system for analyzing a small-volume fluid sample, comprising:
   an automated sample analysis device, said device being configured for use with a sample container, said sample container having a cavity, said cavity having a first volume, the sample container being configured to hold a fluid sample within said cavity;
   a plurality of inserts coupled together in a predetermined configuration, each of said inserts for placement within the cavity of the sample container, each of said inserts having a first outer portion have a first diameter greater than a diameter of the cavity and a second outer portion have a second outer diameter, and an insert cavity configured to hold a fluid sample of no more than about 150 μL, wherein the second outer diameter is sized so that the second outer portion is in slidable contact with the cavity of the sample container said insert cavity having a second volume, said second volume being smaller than said first volume;
   wherein the insert cavity is selected from the group consisting of:
   i) an insert cavity having a wall, said wall comprising an angle effective to provide a taper of said wall of said insert cavity, wherein the taper becomes narrower towards the lower portion
   wherein the insert cavity further comprises a bevel, a floor, and a floor angle formed by said floor and said bevel, wherein the floor angle comprises an angle of between about 100° to about 140°.

2. The system of claim 1, wherein said insert cavity comprises an insert cavity of i), wherein the tapers which become narrower towards the lower portion.

3. The system of claim 1, wherein said predetermined configuration comprises a ring of said inserts.

4. The system of claim 1, wherein said predetermined configuration comprises a disc having said inserts.

5. The system of claim 1, wherein said insert cavity comprises an insert cavity of iii), wherein the ratio of the depth to the width is between about 0.2:1 to about 5:1.

6. The system of claim 1, wherein said insert cavity comprises an insert cavity of iii), wherein the ratio of the depth to the width is about 2:1.

7. The system of claim 1, wherein said insert cavity comprises an insert cavity of iii), wherein the ratio of the depth to the width is about 8:1.

8. The system of claim 1, wherein said insert cavity comprises an insert cavity of an insert disposed within the cavity of an original sample container.

9. The system of claim 1, wherein said sample comprises a diluted sample.

10. The system of claim 9, wherein said diluted sample is diluted by a dilution ratio of greater than about 5:1, where a dilution ratio is defined as the ratio of diluted volume to original volume.

11. The system of claim 1, further comprising a detector configured to provide information about a sample in disposed within the insert cavity, wherein said insert is configured to allow the detection of a signal indicative of the presence of, or quantification of, a target substance in a sample contained within said insert, wherein said detection comprises detection by said detector.

12. The system of claim 11, herein said detector comprises an optical detector disposed externally to said sample container, and wherein said insert is configured to allow the passage of light effective that optical signals indicative of the presence of, or quantification of, a target substance in a sample contained within said insert may be detected by said optical detector.

13. The system of claim 11, wherein said detector comprises a detector selected from an ion-selective electrode, a voltammetric probe, and an amperometric probe.

* * * * *